(12) United States Patent
Broueilh et al.

(10) Patent No.: US 12,203,943 B2
(45) Date of Patent: Jan. 21, 2025

(54) BIOMARKERS OF FAST PROGRESSION OF CHRONIC KIDNEY DISEASE

(71) Applicants: Hoffmann La-Roche Inc., Little Falls, NJ (US); INSERM (Institut National de la Santé et de la Recherche Médicale), Paris (FR)

(72) Inventors: Melanie Broueilh, Paris (FR); Mordi Muorah, Paris (FR); Fabiola Terzi, Paris (FR)

(73) Assignees: Hoffman-La Roche Inc., Little Falls, NJ (US); INSERM (Institut National de la Sante et de la Recherche Medicale), Paris (FR)

( * ) Notice: Subject to any disclaimer, the term of this patent is extended or adjusted under 35 U.S.C. 154(b) by 323 days.

(21) Appl. No.: 17/724,406

(22) Filed: Apr. 19, 2022

(65) Prior Publication Data

US 2022/0252617 A1    Aug. 11, 2022

Related U.S. Application Data

(63) Continuation of application No. 16/546,101, filed on Aug. 20, 2019, now abandoned, which is a continuation of application No. 15/604,888, filed on May 25, 2017, now abandoned, which is a continuation of application No. PCT/EP2015/077504, filed on Nov. 24, 2015.

(30) Foreign Application Priority Data

Nov. 25, 2014 (EP) .................................. 14306879

(51) Int. Cl.
   *G01N 33/68* (2006.01)
   *G01N 33/74* (2006.01)

(52) U.S. Cl.
   CPC ..... *G01N 33/6893* (2013.01); *G01N 33/6863* (2013.01); *G01N 33/74* (2013.01); *G01N 2333/47* (2013.01); *G01N 2333/485* (2013.01); *G01N 2333/495* (2013.01); *G01N 2333/523* (2013.01); *G01N 2800/347* (2013.01); *G01N 2800/52* (2013.01); *G01N 2800/56* (2013.01); *G01N 2800/60* (2013.01)

(58) Field of Classification Search
   CPC ........... G01N 33/6893; G01N 33/6863; G01N 2333/485; G01N 2333/495; G01N 2800/347
   See application file for complete search history.

(56) References Cited

U.S. PATENT DOCUMENTS

| 2014/0079769 A1 | 3/2014 | Terzi |
| 2017/0328914 A1 | 11/2017 | Broueilh et al. |
| 2020/0096523 A1 | 3/2020 | Broueilh et al. |
| 2020/0116740 A1 | 4/2020 | Levitsky et al. |

FOREIGN PATENT DOCUMENTS

| CN | 102292637 A | 12/2011 |
| CN | 102854306 A | 1/2013 |
| CN | 103080743 A | 5/2013 |
| EP | 2622095 B1 | 9/2016 |
| JP | 2012510058 A | 4/2012 |
| WO | 2010058378 A1 | 5/2010 |
| WO | 2010059996 A1 | 5/2010 |
| WO | 2011075744 A1 | 6/2011 |
| WO | 2011162820 A1 | 12/2011 |
| WO | 2012042061 A1 | 4/2012 |

OTHER PUBLICATIONS

Bolignano, D. et al. (2009). "Neutrophil Gelatinase-Associated Lipocalin (NGAL) and Progression of Chronic Kidney Disease," Clin. J. Am. Soc. Nephrol. 4:337-344.

Catania, J.M. et al. (2007). "Role of Matrix Metalloproteinases in Renal Pathophysiologies," Am. J. Physiol. Renal Physiol. 292:F905-F911.

Coresh, J. et al. (2014, e-pub. Jun. 3, 2014). "Decline in Estimated Glomerular Filtration Rate and Subsequent Risk of End-Stage Renal Disease and Mortality," JAMA 311:2518-2531.

Eardley, K.S. et al. (2006, e-pub. Feb. 15, 2006). "The Relationship Between Albuminuria, MCP-I/CCL2, and Interstitial Macrophages in Chronic Kidney Disease" Kidney Int. 69:1189-1197.

Eremina, V. et al. (2003). "Glomerular-Specific Alterations of VEGF-A Expression Lead to Distinct Congenital and Acquired Renal Diseases," J. Clin. Invest. 111(5):707-716.

Fox, C. S., et al. (2012, e-pub. Sep. 24, 2012). "Associations of Kidney Disease Measures With Mortality and End-Stage Renal Disease in Individuals With and Without Diabetes: a Meta-Analysis," Lancet 380:1662-1673.

Ghoul, B. E. et al. (2010). "Urinary Procollagen III Aminoterminal Propeptide (PIIINP): a Fibrotest for the Nephrologist," Clin. J. Am. Soc. Nephrol. 5:205-210.

Gilbert, R. E. et al. (2001). "Urinary Transforming Growth Factor-βin Patients With Diabetic Nephropathy: Implications for the Pathogenesis of Tubulointerstitial Pathology," Nephrol. Dial. Transplant. 16:2442-2443.

Gilbert, R. E. et al. (2003). "Urinary Connective Tissue Growth Factor Excretion in Patients With Type 1 Diabetes and Nephropathy," Diabetes Care 26(9):2632-2636.

Go, A.S. et al. (2004). "Chronic Kidney Disease and the Risks of Death, Cardiovascular Events, and Hospitalization," N. Engl. J. Med. 351:1296-1305.

(Continued)

*Primary Examiner* — Gyan Chandra
(74) *Attorney, Agent, or Firm* — MORRISON & FOERSTER LLP

(57) ABSTRACT

The present invention relates to methods for the prediction of the progression of chronic kidney disease in a patient. More particularly, the invention relates to the early prediction of the fast progression of chronic kidney disease using specific biomarker signatures in urine sample of patients.

5 Claims, 3 Drawing Sheets

Specification includes a Sequence Listing.

(56) References Cited

OTHER PUBLICATIONS

Grandaliano, G. et al. (2000). "MCP-L and EGF Renal Expression and Urine Excretion in Human Congenital Obstructive Nephropathy," Kidney Int. 58:182-192.

Guerrot, D. et al. (2012). "Identification of Periostin as a Critical Marker of Progression/Reversal of Hypertensive Nephropathy." PLoS ONE 7:e31974, 8 pages.

Hang, H. et al. (2014). "Multiplex Bead Array Assay of Plasma Cytokines in Type 2 Diabetes Mellitus With Diabetic Retinopathy," Molecular Vision 20:1137-1145.

Hierget-Rosenthal, S. et al. (2007, e-pub. Apr. 27, 2007). "Increased Urinary Cystatin C Reflects Structural and Functional Renal Tubular Impairment Independent of Glomerular Filtration Rate," Clin. Biochem. 40:946-951.

Humphreys, B.D. et al. (2013). "Chronic Epithelial Kidney Injury Molecule-1 Expression Causes Murine Kidney Fibrosis," J. Clin. Invest. 123(9):4023-4035.

International Search Report and Written Opinion mailed on Jan. 29, 2016, for PCT Application No. PCT/EP2015/077504, filed on Nov. 24, 2015, 11 pages.

Kamijo, A. et al. (2005). "Clinical Evaluation of Urinary Excretion of Liver-Type Fatty Acid-Binding Protein as a Marker for the Monitoring of Chronic Kidney Disease: a Multicenter Trial," J. Lab. Clin. Med. 145:125-133.

Kwon, O. et al. (2010, e-pub. Jun. 12, 2010). "Simultaneous Monitoring of Multiple Urinary Cytokines May Predict Renal and Patient Outcome in Ischemic AKI," Renal Failure 32:699-708.

Lajer, M. et al. (2010, e-pub. Mar. 31, 2010). "Plasma Growth Differentiation Factor-15 Independently Predicts All-Cause and Cardiovascular Mortality As Well As Deterioration of Kidney Function in Type 1 Diabetic Patients With Nephropathy," Diabetes Care 33(7):1567-1572.

Laquari, D. et al. (2011). "TGF-α Mediates Genetic Susceptibility to Chronic Kidney Disease," J. Am. Soc. Nephrol. 22:327-335.

Lautrette, A. et al. (2005, e-pub. Jul. 24, 2005). "Angiotensin II and EGF Receptor Cross-Talk in Chronic Kidney Diseases: a New Therapeutic Approach," Nat. Med. 11(6):867-874.

Levey, A.S. et al. (1999). "A More Accurate Method to Estimate Glomerular Filtration Rate from Serum Creatinine: a New Prediction Equation," Ann. Intern. Med. 130(9):461-470.

Liu, K. D. et al. (2013). "Urine Neutrophil Gelatinase-Associated Lipocalin Levels Do Not Improve Risk Prediction of Progressive Chronic Kidney Disease," Kidney Int. 83, 909-914, 14 pages.

Liu, Y. et al. (2013). "Urinary Interleukin 18 for Detection of Acute Kidney Injury: a Meta-analysis," Am. J. Kidney Dis. 62(6):1058-1067.

Meng, X.-M. et al. (2014, e-pub. Jul. 1, 2014). "Inflammatory Processes in Renal Fibrosis," Nat. Rev. Nephrol. 10:493-503.

Moranne, O. et al. (2009). "Timing of Onset of CKD-Related Metabolic Complications," J. Am. Soc. Nephrol. 20:164-171.

Nakamura, T. et al. (2005). "Effect of Pitavastatin on Urinary Liver-Type Fatty Acid-Binding Protein Levels in Patients With Early Diabetic Nephropathy," Diabetes Care 28(11):2728-2732.

Parikh, C. R. et al. (2005). "Urine IL-18 is an Early Diagnostic Marker for Acute Kidney Injury and Predicts Mortality in the Intensive Care Unit," J. Am. Soc. Nephrol. 16:3046-3052.

Peng, W. et al. (2007). "The Relevance Analysis of Systemic Lupus Erytheomatosus and MCP-1 Level in Body Fluids," Journal of Baotou Medical College 23(6):566-569, (with English Abstract).

Perkins, B.A. et al. (2003). "Regression of Microalbuminuria in Type 1 Diabetes," N. Engl. J. Med. 348:2285-2293.

Rall, L.B. et al. (1985). "Mouse Prepro-Epidermal Growth Factor Synthesis by the Kidney and Other Tissues," Nature 313:228-231.

Rau, S., et al. (2013). "Neutrophil Gelatinase-Associated Lipocalin and End-Stage Renal Disease: It is not all About the Kidneys!," Eur. J. Clin. Invest. 43(9):816-820.

Remuzzi, G. et al. (2005). "The Role of Renin-Angiotensin-Aldosterone System in the Progression of Chronic Kidney Disease," Kidney Int. 68(99): S57-S65.

Riser, B. L. et al. (2003). "Urinary CCN2 (CTGF) as a Possible Predictor of Diabetic Nephropathy: Preliminary Report," Kidney Int. 64:451-458.

Ruggenenti, P. et al. (2012). "Measuring and Estimating GFR and Treatment Effect in ADPKD Patients: Results and Implications of a Longitudinal Cohort Study," PLoS ONE 7:e32533:1-12.

Sakamoto, I. et al. (2009, e-pub. Jan. 14, 2009). "Lymphatic Vessels Develop During Tubulointerstitial Fibrosis," Kidney Int. 75:828-838.

Shankland, S.J. (2006, e-pub. May 10, 2006). "The Podocyte's Response to Injury: Role in Proteinuria and Glomerulosclerosis," Kidney Int. 69:2131-2147.

Shlipak, M.G. et al. (2005). Cardiovascular Mortality Risk in Chronic Kidney Disease: Comparison of Traditional and Novel Risk Factors, JAMA 293(14):1737-1745.

Soylemezoglu, O. et al. (1997). "Urinary and Serum Type III Collagen: Markers of Renal Fibrosis," Nephrol. Dial. Transplant. 12:1883-1889.

Stevens, L.A. et al. (2006). "Surrogate End Points for Clinical Trials of Kidney Disease Progression," Clin. J. Am. Soc. Nephrol. 1:874-884.

Suthanthiran, M. et al. (2009). "Circulating Transforming Growth Factor-[Beta]1 Levels and the Risk for Kidney Disease in African Americans," Kidney Int. 76:72-80.

Tangri, N. et al. (2011). "A Predictive Model for Progression of Chronic Kidney Disease to Kidney Failure," JAMA 305 (15):1553-1559.

Van Vliet, A.I. et al. (2001, e-pub. Nov. 27, 2000). "Distribution of Fibronectin Isoforms in Human Renal Disease," J. Pathol. 193:256-262.

Vianna, H. et al. (2013, e-pub. Nov. 18, 2012). "Cytokines in Chronic Kidney Disease: Potential Link of MCP-1 and Dyslipidemia in Glomerular Diseases," Pediatr. Nephrol. 28:463-469.

Mau, A. et al. (2010). "Lipocalin 2 is Essential for Chronic Kidney Disease Progression in Mice and Humans," J. Clin. Invest. 120:4065-4076.

Von Eynatten, M. et al. (2010). "Urinary L-FABP and Anaemia: Distinct Roles of Urinary Markers in Type 2 Diabetes," Eur. J. Clin. Invest. 40(2):95-102.

Vyletal, P. et al. (2010, e-pub. Nov. 25, 2010). "Uromodulin Biology and Pathophysiology—An Update," Kidney Blood Press. Res. 33:456-475.

Weis, L. et al. (2013). "Renal Function Can Improve at Any Stage of Chronic Kidney Disease," PLoS ONE 8(12):e81835, 1-9.

Yoshino, J. et al. (2003). "Leukemia Inhibitory Factor is Involved in Tubular Regeneration after Experimental Acute Renal Failure," J. Am. Soc. Nephrol. 14:3090-3101.

SEQUENCE LISTING

```
<160> NUMBER OF SEQ ID NOS: 16

<210> SEQ ID NO 1
<211> LENGTH: 1207
<212> TYPE: PRT
<213> ORGANISM: Homo sapiens

<400> SEQUENCE: 1

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
```

180                 185                 190
Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
210                 215                 220

Asn Ser Leu Ile Cys Ser Cys Asp Tyr Asp Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
                260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
                500                 505                 510

Met Val Tyr Ala Leu Asp His Asp Pro Val Glu Asn Lys Ile Tyr Phe
        515                 520                 525

Ala His Thr Ala Leu Lys Trp Ile Glu Arg Ala Asn Met Asp Gly Ser
        530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
                580                 585                 590

Thr Lys Glu Asn Ile Ser Gln Pro Arg Gly Ile Ala Val His Pro Met
        595                 600                 605

-continued

Ala Lys Arg Leu Phe Trp Thr Asp Thr Gly Ile Asn Pro Arg Ile Glu
610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
            645                 650                 655

Tyr Trp Cys Asp Ala Lys Gln Ser Val Ile Glu Met Ala Asn Leu Asp
            660                 665                 670

Gly Ser Lys Arg Arg Leu Thr Gln Asn Asp Val Gly His Pro Phe
        675                 680                 685

Ala Val Ala Val Phe Glu Asp Tyr Val Trp Phe Ser Asp Trp Ala Met
690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val His Pro
            725                 730                 735

Leu Ala Lys Pro Gly Ala Asp Pro Cys Leu Tyr Gln Asn Gly Gly Cys
            740                 745                 750

Glu His Ile Cys Lys Lys Arg Leu Gly Thr Ala Trp Cys Ser Cys Arg
    755                 760                 765

Glu Gly Phe Met Lys Ala Ser Asp Gly Lys Thr Cys Leu Ala Leu Asp
770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
            805                 810                 815

Thr Glu Ser Gln His Met Leu Val Ala Glu Ile Met Val Ser Asp Gln
        820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
            885                 890                 895

Cys Arg Cys Ser Glu Gly Tyr Gln Gly Asp Gly Ile His Cys Leu Asp
        900                 905                 910

Ile Asp Glu Cys Gln Leu Gly Glu His Ser Cys Gly Glu Asn Ala Ser
            915                 920                 925

Cys Thr Asn Thr Glu Gly Gly Tyr Thr Cys Met Cys Ala Gly Arg Leu
930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
            965                 970                 975

Pro Leu Ser His Asp Gly Tyr Cys Leu His Asp Gly Val Cys Met Tyr
            980                 985                 990

Ile Glu Ala Leu Asp Lys Tyr Ala Cys Asn Cys Val Val Gly Tyr Ile
        995                 1000                1005

Gly Glu Arg Cys Gln Tyr Arg Asp Leu Lys Trp Trp Glu Leu Arg
    1010                1015                1020

```
His Ala Gly His Gly Gln Gln Gln Lys Val Ile Val Val Ala Val
    1025                1030                1035

Cys Val Val Val Leu Val Met Leu Leu Leu Leu Ser Leu Trp Gly
    1040                1045                1050

Ala His Tyr Tyr Arg Thr Gln Lys Leu Leu Ser Lys Asn Pro Lys
    1055                1060                1065

Asn Pro Tyr Glu Ser Ser Arg Asp Val Arg Ser Arg Arg Pro
    1070                1075                1080

Ala Asp Thr Glu Asp Gly Met Ser Ser Cys Pro Gln Pro Trp Phe
    1085                1090                1095

Val Val Ile Lys Glu His Gln Asp Leu Lys Asn Gly Gly Gln Pro
    1100                1105                1110

Val Ala Gly Glu Asp Gly Gln Ala Ala Asp Gly Ser Met Gln Pro
    1115                1120                1125

Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170

Thr Leu Glu Gly Gly Val Glu Lys Pro His Ser Leu Leu Ser Ala
    1175                1180                1185

Asn Pro Leu Trp Gln Gln Arg Ala Leu Asp Pro Pro His Gln Met
    1190                1195                1200

Glu Leu Thr Gln
    1205

<210> SEQ ID NO 2
<211> LENGTH: 308
<212> TYPE: PRT
<213> ORGANISM: Homo sapiens

<400> SEQUENCE: 2

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
                35                  40                  45

Glu Asp Ser Arg Phe Arg Glu Leu Arg Lys Arg Tyr Glu Asp Leu Leu
            50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                    85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                    165                 170                 175
```

```
Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
            195                 200                 205

Arg Cys Cys Arg Leu His Thr Val Arg Ala Ser Leu Glu Asp Leu Gly
210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
            275                 280                 285

Asp Thr Gly Val Ser Leu Gln Thr Tyr Asp Asp Leu Leu Ala Lys Asp
        290                 295                 300

Cys His Cys Ile
305

<210> SEQ ID NO 3
<211> LENGTH: 160
<212> TYPE: PRT
<213> ORGANISM: Homo sapiens

<400> SEQUENCE: 3

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
            20                  25                  30

Asp Pro Pro Val Ala Ala Val Val Ser His Phe Asn Asp Cys Pro
                35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
        115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Val Val
145                 150                 155                 160

<210> SEQ ID NO 4
<211> LENGTH: 99
<212> TYPE: PRT
<213> ORGANISM: Homo sapiens

<400> SEQUENCE: 4

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30
```

```
Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
 50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                 85                  90                  95

Pro Lys Thr

<210> SEQ ID NO 5
<211> LENGTH: 127
<212> TYPE: PRT
<213> ORGANISM: Homo sapiens

<400> SEQUENCE: 5

Met Ser Phe Ser Gly Lys Tyr Gln Leu Gln Ser Gln Glu Asn Phe Glu
 1               5                  10                  15

Ala Phe Met Lys Ala Ile Gly Leu Pro Glu Glu Leu Ile Gln Lys Gly
                 20                  25                  30

Lys Asp Ile Lys Gly Val Ser Glu Ile Val Gln Asn Gly Lys His Phe
             35                  40                  45

Lys Phe Thr Ile Thr Ala Gly Ser Lys Val Ile Gln Asn Glu Phe Thr
 50                  55                  60

Val Gly Glu Glu Cys Glu Leu Glu Thr Met Thr Gly Glu Lys Val Lys
 65                  70                  75                  80

Thr Val Val Gln Leu Glu Gly Asp Asn Lys Leu Val Thr Thr Phe Lys
                 85                  90                  95

Asn Ile Lys Ser Val Thr Glu Leu Asn Gly Asp Ile Ile Thr Asn Thr
             100                 105                 110

Met Thr Leu Gly Asp Ile Val Phe Lys Arg Ile Ser Lys Arg Ile
         115                 120                 125

<210> SEQ ID NO 6
<211> LENGTH: 146
<212> TYPE: PRT
<213> ORGANISM: Homo sapiens

<400> SEQUENCE: 6

Met Ala Gly Pro Leu Arg Ala Pro Leu Leu Leu Ala Ile Leu Ala
 1               5                  10                  15

Val Ala Leu Ala Val Ser Pro Ala Ala Gly Ser Ser Pro Gly Lys Pro
                 20                  25                  30

Pro Arg Leu Val Gly Gly Pro Met Asp Ala Ser Val Glu Glu Glu Gly
             35                  40                  45

Val Arg Arg Ala Leu Asp Phe Ala Val Gly Glu Tyr Asn Lys Ala Ser
 50                  55                  60

Asn Asp Met Tyr His Ser Arg Ala Leu Gln Val Val Arg Ala Arg Lys
 65                  70                  75                  80

Gln Ile Val Ala Gly Val Asn Tyr Phe Leu Asp Val Glu Leu Gly Arg
                 85                  90                  95

Thr Thr Cys Thr Lys Thr Gln Pro Asn Leu Asp Asn Cys Pro Phe His
             100                 105                 110

Asp Gln Pro His Leu Lys Arg Lys Ala Phe Cys Ser Phe Gln Ile Tyr
         115                 120                 125
```

```
Ala Val Pro Trp Gln Gly Thr Met Thr Leu Ser Lys Ser Thr Cys Gln
    130                 135                 140

Asp Ala
145

<210> SEQ ID NO 7
<211> LENGTH: 2386
<212> TYPE: PRT
<213> ORGANISM: Homo sapiens

<400> SEQUENCE: 7

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350
```

```
Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
            450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
            690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765
```

```
Pro Ser Thr Ala Thr Ser Val Asn Ile Pro Asp Leu Leu Pro Gly Arg
770             775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Val Arg Trp Ser
        820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
```

-continued

```
            1175                1180                1185
Gly Val Leu Thr Val Ser Trp Glu Arg Ser Thr Thr Pro Asp Ile
            1190                1195                1200
Thr Gly Tyr Arg Ile Thr Thr Pro Thr Asn Gly Gln Gln Gly
            1205                1210                1215
Asn Ser Leu Glu Glu Val Val His Ala Asp Gln Ser Ser Cys Thr
            1220                1225                1230
Phe Asp Asn Leu Ser Pro Gly Leu Glu Tyr Asn Val Ser Val Tyr
            1235                1240                1245
Thr Val Lys Asp Asp Lys Glu Ser Val Pro Ile Ser Asp Thr Ile
            1250                1255                1260
Ile Pro Ala Val Pro Pro Thr Asp Leu Arg Phe Thr Asn Ile
            1265                1270                1275
Gly Pro Asp Thr Met Arg Val Thr Trp Ala Pro Pro Ser Ile
            1280                1285                1290
Asp Leu Thr Asn Phe Leu Val Arg Tyr Ser Pro Val Lys Asn Glu
            1295                1300                1305
Glu Asp Val Ala Glu Leu Ser Ile Ser Pro Ser Asp Asn Ala Val
            1310                1315                1320
Val Leu Thr Asn Leu Leu Pro Gly Thr Glu Tyr Val Val Ser Val
            1325                1330                1335
Ser Ser Val Tyr Glu Gln His Glu Ser Thr Pro Leu Arg Gly Arg
            1340                1345                1350
Gln Lys Thr Gly Leu Asp Ser Pro Thr Gly Ile Asp Phe Ser Asp
            1355                1360                1365
Ile Thr Ala Asn Ser Phe Thr Val His Trp Ile Ala Pro Arg Ala
            1370                1375                1380
Thr Ile Thr Gly Tyr Arg Ile Arg His His Pro Glu His Phe Ser
            1385                1390                1395
Gly Arg Pro Arg Glu Asp Arg Val Pro His Ser Arg Asn Ser Ile
            1400                1405                1410
Thr Leu Thr Asn Leu Thr Pro Gly Thr Glu Tyr Val Val Ser Ile
            1415                1420                1425
Val Ala Leu Asn Gly Arg Glu Glu Ser Pro Leu Leu Ile Gly Gln
            1430                1435                1440
Gln Ser Thr Val Ser Asp Val Pro Arg Asp Leu Glu Val Val Ala
            1445                1450                1455
Ala Thr Pro Thr Ser Leu Leu Ile Ser Trp Asp Ala Pro Ala Val
            1460                1465                1470
Thr Val Arg Tyr Tyr Arg Ile Thr Tyr Gly Glu Thr Gly Gly Asn
            1475                1480                1485
Ser Pro Val Gln Glu Phe Thr Val Pro Gly Ser Lys Ser Thr Ala
            1490                1495                1500
Thr Ile Ser Gly Leu Lys Pro Gly Val Asp Tyr Thr Ile Thr Val
            1505                1510                1515
Tyr Ala Val Thr Gly Arg Gly Asp Ser Pro Ala Ser Ser Lys Pro
            1520                1525                1530
Ile Ser Ile Asn Tyr Arg Thr Glu Ile Asp Lys Pro Ser Gln Met
            1535                1540                1545
Gln Val Thr Asp Val Gln Asp Asn Ser Ile Ser Val Lys Trp Leu
            1550                1555                1560
Pro Ser Ser Ser Pro Val Thr Gly Tyr Arg Val Thr Thr Thr Pro
            1565                1570                1575
```

```
Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635

Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
    1685                1690                1695

Thr Val Ser Val Val Ala Leu His Asp Asp Met Glu Ser Gln Pro
    1700                1705                1710

Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr
    1730                1735                1740

Pro Pro Asn Val Gln Leu Thr Gly Tyr Arg Val Arg Val Thr Pro
    1745                1750                1755

Lys Glu Lys Thr Gly Pro Met Lys Glu Ile Asn Leu Ala Pro Asp
    1760                1765                1770

Ser Ser Ser Val Val Val Ser Gly Leu Met Val Ala Thr Lys Tyr
    1775                1780                1785

Glu Val Ser Val Tyr Ala Leu Lys Asp Thr Leu Thr Ser Arg Pro
    1790                1795                1800

Ala Gln Gly Val Val Thr Thr Leu Glu Asn Val Ser Pro Pro Arg
    1805                1810                1815

Arg Ala Arg Val Thr Asp Ala Thr Glu Thr Thr Ile Thr Ile Ser
    1820                1825                1830

Trp Arg Thr Lys Thr Glu Thr Ile Thr Gly Phe Gln Val Asp Ala
    1835                1840                1845

Val Pro Ala Asn Gly Gln Thr Pro Ile Gln Arg Thr Ile Lys Pro
    1850                1855                1860

Asp Val Arg Ser Tyr Thr Ile Thr Gly Leu Gln Pro Gly Thr Asp
    1865                1870                1875

Tyr Lys Ile Tyr Leu Tyr Thr Leu Asn Asp Asn Ala Arg Ser Ser
    1880                1885                1890

Pro Val Val Ile Asp Ala Ser Thr Ala Ile Asp Ala Pro Ser Asn
    1895                1900                1905

Leu Arg Phe Leu Ala Thr Thr Pro Asn Ser Leu Leu Val Ser Trp
    1910                1915                1920

Gln Pro Pro Arg Ala Arg Ile Thr Gly Tyr Ile Ile Lys Tyr Glu
    1925                1930                1935

Lys Pro Gly Ser Pro Pro Arg Glu Val Val Pro Arg Pro Arg Pro
    1940                1945                1950

Gly Val Thr Glu Ala Thr Ile Thr Gly Leu Glu Pro Gly Thr Glu
    1955                1960                1965
```

```
Tyr Thr Ile Tyr Val Ile Ala Leu Lys Asn Asn Gln Lys Ser Glu
1970             1975                 1980

Pro Leu Ile Gly Arg Lys Lys Thr Asp Glu Leu Pro Gln Leu Val
1985             1990                 1995

Thr Leu Pro His Pro Asn Leu His Gly Pro Glu Ile Leu Asp Val
2000             2005                 2010

Pro Ser Thr Val Gln Lys Thr Pro Phe Val Thr His Pro Gly Tyr
2015             2020                 2025

Asp Thr Gly Asn Gly Ile Gln Leu Pro Gly Thr Ser Gly Gln Gln
2030             2035                 2040

Pro Ser Val Gly Gln Gln Met Ile Phe Glu Glu His Gly Phe Arg
2045             2050                 2055

Arg Thr Thr Pro Pro Thr Thr Ala Thr Pro Ile Arg His Arg Pro
2060             2065                 2070

Arg Pro Tyr Pro Pro Asn Val Gly Glu Glu Ile Gln Ile Gly His
2075             2080                 2085

Ile Pro Arg Glu Asp Val Asp Tyr His Leu Tyr Pro His Gly Pro
2090             2095                 2100

Gly Leu Asn Pro Asn Ala Ser Thr Gly Gln Glu Ala Leu Ser Gln
2105             2110                 2115

Thr Thr Ile Ser Trp Ala Pro Phe Gln Asp Thr Ser Glu Tyr Ile
2120             2125                 2130

Ile Ser Cys His Pro Val Gly Thr Asp Glu Glu Pro Leu Gln Phe
2135             2140                 2145

Arg Val Pro Gly Thr Ser Thr Ser Ala Thr Leu Thr Gly Leu Thr
2150             2155                 2160

Arg Gly Ala Thr Tyr Asn Val Ile Val Glu Ala Leu Lys Asp Gln
2165             2170                 2175

Gln Arg His Lys Val Arg Glu Glu Val Val Thr Val Gly Asn Ser
2180             2185                 2190

Val Asn Glu Gly Leu Asn Gln Pro Thr Asp Asp Ser Cys Phe Asp
2195             2200                 2205

Pro Tyr Thr Val Ser His Tyr Ala Val Gly Asp Glu Trp Glu Arg
2210             2215                 2220

Met Ser Glu Ser Gly Phe Lys Leu Leu Cys Gln Cys Leu Gly Phe
2225             2230                 2235

Gly Ser Gly His Phe Arg Cys Asp Ser Ser Arg Trp Cys His Asp
2240             2245                 2250

Asn Gly Val Asn Tyr Lys Ile Gly Glu Lys Trp Asp Arg Gln Gly
2255             2260                 2265

Glu Asn Gly Gln Met Met Ser Cys Thr Cys Leu Gly Asn Gly Lys
2270             2275                 2280

Gly Glu Phe Lys Cys Asp Pro His Glu Ala Thr Cys Tyr Asp Asp
2285             2290                 2295

Gly Lys Thr Tyr His Val Gly Glu Gln Trp Gln Lys Glu Tyr Leu
2300             2305                 2310

Gly Ala Ile Cys Ser Cys Thr Cys Phe Gly Gly Gln Arg Gly Trp
2315             2320                 2325

Arg Cys Asp Asn Cys Arg Arg Pro Gly Gly Glu Pro Ser Pro Glu
2330             2335                 2340

Gly Thr Thr Gly Gln Ser Tyr Asn Gln Tyr Ser Gln Arg Tyr His
2345             2350                 2355

Gln Arg Thr Asn Thr Asn Val Asn Cys Pro Ile Glu Cys Phe Met
```

```
                2360                2365                2370
Pro Leu Asp Val Gln Ala Asp Arg Glu Asp Ser Arg Glu
    2375                2380                2385

<210> SEQ ID NO 8
<211> LENGTH: 359
<212> TYPE: PRT
<213> ORGANISM: Homo sapiens

<400> SEQUENCE: 8

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Thr Thr Thr
145                 150                 155                 160

Val Pro Thr Thr Met Ser Ile Pro Thr Thr Thr Val Leu Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350
```

Asn Ser Leu Tyr Ala Thr Asp
        355

<210> SEQ ID NO 9
<211> LENGTH: 198
<212> TYPE: PRT
<213> ORGANISM: Homo sapiens

<400> SEQUENCE: 9

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195

<210> SEQ ID NO 10
<211> LENGTH: 207
<212> TYPE: PRT
<213> ORGANISM: Homo sapiens

<400> SEQUENCE: 10

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

```
Gln Asp Gly Leu Leu His Ile Thr Thr Cys Ser Phe Val Ala Pro Trp
            115                 120                 125

Asn Ser Leu Ser Leu Ala Gln Arg Arg Gly Phe Thr Lys Thr Tyr Thr
130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
            165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
            195                 200                 205

<210> SEQ ID NO 11
<211> LENGTH: 640
<212> TYPE: PRT
<213> ORGANISM: Homo sapiens

<400> SEQUENCE: 11

Met Gly Gln Pro Ser Leu Thr Trp Met Leu Met Val Val Ala Ser
1               5                   10                  15

Trp Phe Ile Thr Thr Ala Ala Thr Asp Thr Ser Glu Ala Arg Trp Cys
                20                  25                  30

Ser Glu Cys His Ser Asn Ala Thr Cys Thr Glu Asp Glu Ala Val Thr
            35                  40                  45

Thr Cys Thr Cys Gln Glu Gly Phe Thr Gly Asp Gly Leu Thr Cys Val
        50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
            100                 105                 110

Ala Glu Pro Gly Leu Ser His Cys His Ala Leu Ala Thr Cys Val Asn
        115                 120                 125

Val Val Gly Ser Tyr Leu Cys Val Cys Pro Ala Gly Tyr Arg Gly Asp
130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
                165                 170                 175

His Arg Thr Leu Asp Glu Tyr Trp Arg Ser Thr Glu Tyr Gly Glu Gly
            180                 185                 190

Tyr Ala Cys Asp Thr Asp Leu Arg Gly Trp Tyr Arg Phe Val Gly Gln
        195                 200                 205

Gly Gly Ala Arg Met Ala Glu Thr Cys Val Pro Val Leu Arg Cys Asn
210                 215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
                245                 250                 255

Leu Trp Asp Ala Ser Val Gln Val Lys Ala Cys Ala Gly Gly Tyr Tyr
            260                 265                 270

Val Tyr Asn Leu Thr Ala Pro Pro Glu Cys His Leu Ala Tyr Cys Thr
        275                 280                 285
```

Asp Pro Ser Ser Val Glu Gly Thr Cys Glu Glu Cys Ser Ile Asp Glu
        290                 295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
                325                 330                 335

Ala Asn Asp Met Lys Val Ser Leu Gly Lys Cys Gln Leu Lys Ser Leu
            340                 345                 350

Gly Phe Asp Lys Val Phe Met Tyr Leu Ser Asp Ser Arg Cys Ser Gly
        355                 360                 365

Phe Asn Asp Arg Asp Asn Arg Asp Trp Val Ser Val Val Thr Pro Ala
370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Ile Arg Asp
                405                 410                 415

Leu Asn Ile Lys Ile Asn Phe Ala Cys Ser Tyr Pro Leu Asp Met Lys
            420                 425                 430

Val Ser Leu Lys Thr Ala Leu Gln Pro Met Val Ser Ala Leu Asn Ile
        435                 440                 445

Arg Val Gly Gly Thr Gly Met Phe Thr Val Arg Met Ala Leu Phe Gln
450                 455                 460

Thr Pro Ser Tyr Thr Gln Pro Tyr Gln Gly Ser Ser Val Thr Leu Ser
465                 470                 475                 480

Thr Glu Ala Phe Leu Tyr Val Gly Thr Met Leu Asp Gly Gly Asp Leu
                485                 490                 495

Ser Arg Phe Ala Leu Leu Met Thr Asn Cys Tyr Ala Thr Pro Ser Ser
            500                 505                 510

Asn Ala Thr Asp Pro Leu Lys Tyr Phe Ile Ile Gln Asp Arg Cys Pro
        515                 520                 525

His Thr Arg Asp Ser Thr Ile Gln Val Val Glu Asn Gly Glu Ser Ser
530                 535                 540

Gln Gly Arg Phe Ser Val Gln Met Phe Arg Phe Ala Gly Asn Tyr Asp
545                 550                 555                 560

Leu Val Tyr Leu His Cys Glu Val Tyr Leu Cys Asp Thr Met Asn Glu
                565                 570                 575

Lys Cys Lys Pro Thr Cys Ser Gly Thr Arg Phe Arg Ser Gly Ser Val
            580                 585                 590

Ile Asp Gln Ser Arg Val Leu Asn Leu Gly Pro Ile Thr Arg Lys Gly
        595                 600                 605

Val Gln Ala Thr Val Ser Arg Ala Phe Ser Ser Leu Gly Leu Leu Lys
610                 615                 620

Val Trp Leu Pro Leu Leu Leu Ser Ala Thr Leu Thr Leu Thr Phe Gln
625                 630                 635                 640

<210> SEQ ID NO 12
<211> LENGTH: 232
<212> TYPE: PRT
<213> ORGANISM: Homo sapiens

<400> SEQUENCE: 12

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly

```
                20                  25                  30
Gly Gly Gln Asn His His Glu Val Val Lys Phe Met Asp Val Tyr Gln
            35                  40                  45
Arg Ser Tyr Cys His Pro Ile Glu Thr Leu Val Asp Ile Phe Gln Glu
        50                  55                  60
Tyr Pro Asp Glu Ile Glu Tyr Ile Phe Lys Pro Ser Cys Val Pro Leu
 65                  70                  75                  80
Met Arg Cys Gly Gly Cys Cys Asn Asp Glu Gly Leu Glu Cys Val Pro
                85                  90                  95
Thr Glu Glu Ser Asn Ile Thr Met Gln Ile Met Arg Ile Lys Pro His
            100                 105                 110
Gln Gly Gln His Ile Gly Glu Met Ser Phe Leu Gln His Asn Lys Cys
        115                 120                 125
Glu Cys Arg Pro Lys Lys Asp Arg Ala Arg Gln Glu Lys Lys Ser Val
    130                 135                 140
Arg Gly Lys Gly Lys Gly Gln Lys Arg Lys Arg Lys Lys Ser Arg Tyr
145                 150                 155                 160
Lys Ser Trp Ser Val Tyr Val Gly Ala Arg Cys Cys Leu Met Pro Trp
                165                 170                 175
Ser Leu Pro Gly Pro His Pro Cys Gly Pro Cys Ser Glu Arg Arg Lys
            180                 185                 190
His Leu Phe Val Gln Asp Pro Gln Thr Cys Lys Cys Ser Cys Lys Asn
        195                 200                 205
Thr Asp Ser Arg Cys Lys Ala Arg Gln Leu Glu Leu Asn Glu Arg Thr
    210                 215                 220
Cys Arg Cys Asp Lys Pro Arg Arg
225                 230

<210> SEQ ID NO 13
<211> LENGTH: 314
<212> TYPE: PRT
<213> ORGANISM: Homo sapiens

<400> SEQUENCE: 13

Met Arg Ile Ala Val Ile Cys Phe Cys Leu Leu Gly Ile Thr Cys Ala
 1                   5                  10                  15
Ile Pro Val Lys Gln Ala Asp Ser Gly Ser Ser Glu Glu Lys Gln Leu
            20                  25                  30
Tyr Asn Lys Tyr Pro Asp Ala Val Ala Thr Trp Leu Asn Pro Asp Pro
        35                  40                  45
Ser Gln Lys Gln Asn Leu Leu Ala Pro Gln Asn Ala Val Ser Ser Glu
    50                  55                  60
Glu Thr Asn Asp Phe Lys Gln Glu Thr Leu Pro Ser Lys Ser Asn Glu
 65                  70                  75                  80
Ser His Asp His Met Asp Asp Met Asp Glu Asp Asp Asp His
                85                  90                  95
Val Asp Ser Gln Asp Ser Ile Asp Ser Asn Asp Ser Asp Asp Val Asp
            100                 105                 110
Asp Thr Asp Asp Ser His Gln Ser Asp Glu Ser His His Ser Asp Glu
        115                 120                 125
Ser Asp Glu Leu Val Thr Asp Phe Pro Thr Asp Leu Pro Ala Thr Glu
    130                 135                 140
Val Phe Thr Pro Val Val Pro Thr Val Asp Thr Tyr Asp Gly Arg Gly
145                 150                 155                 160
```

```
Asp Ser Val Val Tyr Gly Leu Arg Ser Lys Ser Lys Phe Arg Arg
            165                 170                 175

Pro Asp Ile Gln Tyr Pro Asp Ala Thr Asp Glu Asp Ile Thr Ser His
        180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
        210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
        290                 295                 300

Glu Leu Asp Ser Ala Ser Ser Glu Val Asn
305                 310

<210> SEQ ID NO 14
<211> LENGTH: 212
<212> TYPE: PRT
<213> ORGANISM: Homo sapiens

<400> SEQUENCE: 14

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
        210
```

<210> SEQ ID NO 15
<211> LENGTH: 202
<212> TYPE: PRT
<213> ORGANISM: Homo sapiens

<400> SEQUENCE: 15

Met Lys Val Leu Ala Ala Gly Val Val Pro Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
        195                 200

<210> SEQ ID NO 16
<211> LENGTH: 707
<212> TYPE: PRT
<213> ORGANISM: Homo sapiens

<400> SEQUENCE: 16

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

```
Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Pro Gln Pro Thr Ala Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
    530                 535                 540
```

-continued

```
Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
        610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
            690                 695                 700

Pro Glu Asp
705
```

BIOMARKERS OF FAST PROGRESSION OF CHRONIC KIDNEY DISEASE

CROSS-REFERENCE TO RELATED APPLICATIONS

This application is a continuation of U.S. patent application Ser. No. 16/546,101 filed Aug. 20, 2019, which is a continuation of U.S. patent application Ser. No. 15/604,888, filed May 25, 2017, now abandoned, which is a continuation of International Patent Application No. PCT/EP2015/077504, having an international filing date of Nov. 24, 2015, the entire contents of which are incorporated herein by reference, and which claims benefit under 35 U.S.C. § 119 to European Patent Application No. 14306879.9, filed on Nov. 25, 2014.

SEQUENCE LISTING

The content of the following submission on ASCII text file is incorporated herein by reference in its entirety: a computer readable form (CRF) of the Sequence Listing (file name: 146392061203SEQLIST. TXT, date recorded: Apr. 19, 2022, size: 66,108 bytes).

FIELD OF THE INVENTION

The present invention relates to methods for the prediction of the progression of chronic kidney disease in a patient. More particularly, the invention relates to the early prediction of the fast progression of chronic kidney disease using specific biomarker signatures in urine sample of patients.

BACKGROUND OF THE INVENTION

Chronic Kidney Disease (CKD) currently affects about 10% of the Western population and the incidence is thought to be increasing worldwide. Low glomerular filtration rate (GFR) is associated with increased risk of death from cardiovascular as well as age standardized all-cause mortality.[1,2] This increased risk of death arises even prior to patients reaching end stage renal disease (ESRD)[1]. CKD is thus a significant public health problem. Some patients with CKD will progress rapidly on to end stage renal disease (ESRD) and are therefore at higher risk, while in others the CKD may remain stable or even improve.[3] Identifying those patients likely to progress is paramount to stratification. Albuminuria is a good predictor of CKD progression.[4] Albuminuria can however regress in spite of on-going CKD.[5]

There are a number of effectors which may play a role in CKD progression and could be potential candidates as biomarker of kidney progression.

Transforming growth factor-β (TGF-β)[6] pathway and its downstream effector connective tissue growth factor (CTGF)[7,8] are known major driving factors of matrix synthesis and potential factor of fibrosis development. Extracellular matrix (ECM) accumulation, which is the building block of fibrosis, consists of molecules such as collagen III so we studied Procollagen III amino terminal propeptide (PIIINP)[9,10] (an indirect index of the amount of collagen is synthesised) as well as fibronectin 1 (FN1)[11] and periostin[12]—two other significant ECM molecules. As their names imply, other molecules involved in ECM remodelling for study are matrix metalloprotease 9 (MMP9) and tissue inhibitor of metalloprotease 1 (TIMP1) which respectively breakdown ECM and inhibit this break down action[11].

Inflammatory processes are thought to play important roles in driving eventual fibrosis. From an inflammation point of view, a number of inflammatory chemokines and cytokines may be involved: monocyte chemoattractant protein 1 (MCP1)[14], osteopontin[15], Interleukin 18 (IL18)[16], IL6[17], and leukocyte inhibitory factor (LIF)[18] and growth and differentiation factor 15 (GDF15)[19]. Growth factors such as ligands of the epidermal growth factor (EGF) receptor (EGFR) have a role in cell growth and proliferation. Ligands such as EGF and transforming growth factor alpha (TGF-α) in the pathophysiology may have a role in CKD[20]. Neutrophil gelatinase associated lipocalin can amongst its many other roles act downstream of the EGFR[21]. The vascular endothelial growth factors A (VEGFA)[22] and C (VEGFC)[23] are growth factors implicated in angiogenesis and lymphangiogenesis both of which also have identified roles in CKD progression.

Other molecules are more specific to the kidney structure and function and are expressed at varying levels depending on the degree of kidney damage. Fatty Acid Binding Protein 1 (FABP1)[24-26] is mainly expressed in the proximal tubule. Kidney injury molecule 1 (KIM1) is also expressed on the renal tubules but exclusively in disease state.[27] EGF is also expressed in the distal tubules[28]. Cystatin C is a 13.4 kDa cysteine protease inhibitor, freely filtered in the glomerulus and reabsorbed in the tubules[29] and thus elevated urinary levels might suggest tubular damage. Uromodulin is expressed in the loop of Henle and is secreted into the urine[30].

Despite this physiopathological information, there is no reliable biomarker signature for use in prediction of fast progression.

In a large study by Tangri et al. involving a total of 8391 patients in CKD stages 3 to 5, a predictive model for CKD progression using routinely measured indices such as plasma albumin, calcium, phosphate, bicarbonate, albuminuria and taking account of age, gender and baseline estimated glomerular flgration rate (eGFR) was shown to be predictive of CKD progressing to renal failure33. The main outcome measure here was requirement for renal replacement therapy.

Other groups have looked at other models to predict CKD progression employing for the most part the less accurate eGFR rather the measured glomerular filtration rate (mGFR) gold standard. The eGFR is clearly easier and cheaper to measure but the fact that the findings are not completely reproduced using eGFR equation is not surprising. The inaccuracy of eGFR in the face of mGFR has already been reported due to the lack of sensitivity of the eGFR43. The error is further amplified when looking at progression where two or more GFRs have to be taken into account.

The detection of albuminuria together with the demographic risk factors remain however the standard approach. Increasing prediction accuracy by adding in reliable biomarkers, particularly urinary biomarkers, would thus be useful. In particular, there is an increasing need in the art for an in vitro early detection method of patients at risk of fast progression of chronic kidney disease.

The present invention thus fulfills this need as disclosing specific combinations of urinary biomarkers associated to CKD progression and providing novel prediction methods of CKD progression and their kits.

SUMMARY OF THE INVENTION

The present invention relates to an in vitro method for the prediction of fast progression of chronic kidney disease in a subject, comprising the steps of evaluating the expression of one or more biomarkers in a biological sample obtained from said subject, wherein said one or more biomarkers are selected from the group consisting of transforming growth factor alpha (TGF-α), epidermal growth factor (EGF), and monocyte chemoattractant protein 1 (MCP1).

In specific embodiments, the prediction method of the invention comprises evaluating at least the expressions of EGF, MCP1, and TGF-α, and, optionally, Neutrophil Gelatinase-associated Lipocalin (NGAL).

In other specific embodiments that may be combined with the previous embodiments, the evaluating step include (a) quantifying the expression of one or more of the selected biomarkers in a biological sample obtained from said subject to obtain an expression value for each quantified biomarker, and (b) comparing said expression value obtained at step (a) to a corresponding control value, wherein an expression value of EGF below a control value and/or an expression value of MCP1 above a control value and/or an expression value of TGF-α above a control value, and/or an expression value of NGAL above a control value, indicates that the human subject is at increased risk of fast progression.

In other specific embodiments that may be combined with the previous embodiments, the expression of one or more biomarkers selected from the group consisting of: Growth and Differentiation Factor 15 (GDF15), Neutrophil Gelatinase-associated Lipocalin (NGAL), Cystatin C, Fatty Acid Binding Protein (FABP), Fibronectin, Kidney Injury Molecule 1 (KIM1), Osteopontin, Tissue Inhibitor of Mettaloprotease 1 (TIMP1), Uromodulin and Vascular Endothelial Growth Factor A (VEGFA), Interleukin-6 (IL6), Leukemia Inhibitory Factor (LIF), Matrix Metallopeptidase 9 (MMP9) is further evaluated.

In other specific embodiments that may be combined with the previous embodiments, said biological sample for use in the method is urine or serum sample.

In other specific embodiments that may be combined with the previous embodiments, protein expression of each biomarker is evaluated in the biological sample, for example as quantified in an immunoassay.

In other specific embodiments that may be combined with the previous embodiments, said subject predicted of fast progression is then selected for treatment with a therapeutic agent for treating chronic kidney disease.

The invention further relates to an in vitro method for monitoring the efficacy of a therapeutic agent for treating chronic kidney disease in a subject, comprising evaluating the expressions of biomarkers in a biological sample of said subject, wherein said biomarkers are EGF, MCP1, and TGF-α and, optionally, evaluating the expression of NGAL.

In other specific embodiments that may be combined with the previous embodiment, a first evaluating step prior to treating chronic kidney disease is carried out and is then repeated during or after said treatment step, wherein a change in the expressions of said biomarkers is indicative of a response to said treatment.

The invention further relates to a kit for carrying out any one of the above methods of the invention, said kit comprising means for quantifying protein expression of at least the following biomarker: EGF, MCP1, and TGF-α, and, optionally, means for quantifying protein expression of NGAL.

In other specific embodiments that may be combined with the previous embodiments, said means for quantifying protein expression include unlabelled antibodies specific of each biomarker and, optionally, second labeled antibodies for detecting said biomarker/unlabelled antibodies in an immunoassay.

For example, in a more specific embodiment, the kits of the invention, for use in an immunoassay, comprises:
(i) antibodies specific of EGF;
(ii) antibodies specific of MCP1; and,
(iii) antibodies specific of TGF-α,
(iv) optionally antibodies specific of NGAL.

In specific embodiments, said antibodies comprised in the kit are immobilized on a support. In other specific embodiments, said antibodies comprised in the kit are conjugated to reporter molecule(s).

Squares represent patients in whom there is concordance in rates of progression using either method: filled squares are fast progressors (n=38) and empty squares are slow progressors (n=131). The circles represent patients in whom there is disconcordance in the two methods: filled circles are fast progressors by mGFR but not eGFR (n=30) and empty circles are fast progressors by eGFR but not mGFR (n=30). The grey line shows the line of regression (pearson's correlation coefficient r=0.5). 5 outliers were not represented here (>50 and <−50% change in baseline mGFR/year). *eGFR was estimated using the modification of diet in renal disease (MDRD) equation.

Figure 3:
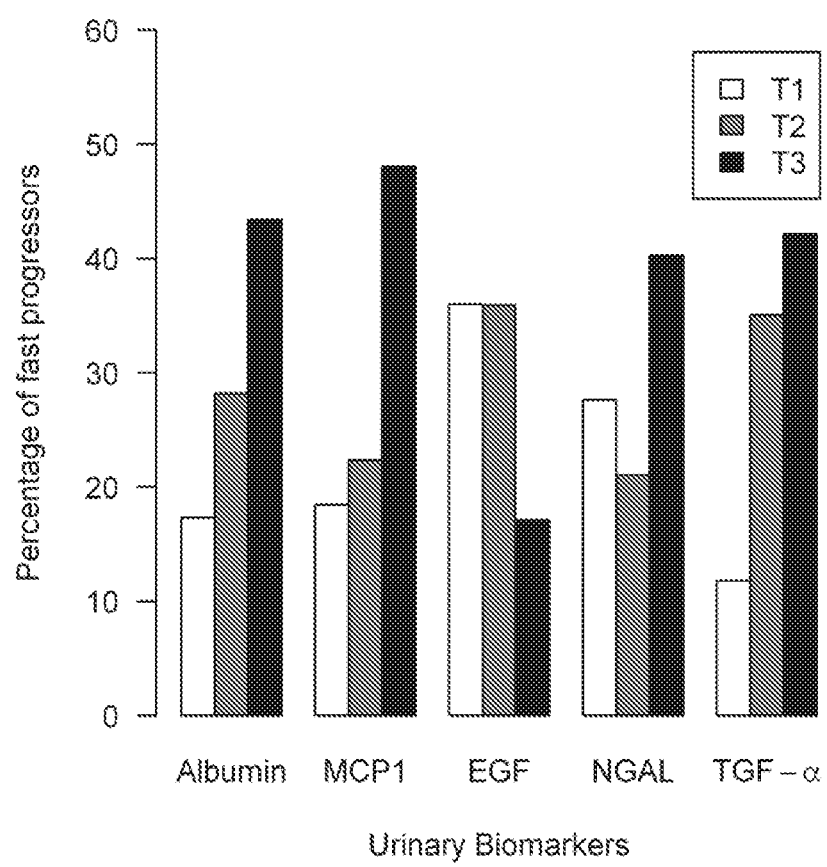

FIG. 3: Biomarker Tertiles of biomarkers in the signature.

Percentage of fast progressors (>10% loss in measured glomerular filtration rate (mGFR) per year) in each of the tertiles of urinary biomarkers in Model 5. Albumin tertiles T1: <3.58; T2: 3.58-33.02; and T3: ≥33.02 mg/mmol. Epidermal growth factor (EGF) tertiles T1: <0.46; T2: 0.46-0.81; and T3: ≥0.81 µg/mmol; monocyte chemoattractant protein (MCP1) tertiles T1: <17.7; T2: 17.7-35.6; and T3: ≥32.6 ng/mmol; neutrophil gelatinase associated lipocalin (NGAL) tertiles T1: <0.26; T2: 0.26-0.76; and T3: ≥0.76 µg/mmol; and transforming growth factor-α (TGF-α) tertiles T1: <0.30; T2: 0.30-0.47; and T3: ≥0.47 ng/mmol. A J-shaped distribution of tertiles can be observed for NGAL

DETAILED DESCRIPTION OF THE INVENTION

Methods allowing an early prediction of the likelihood of fast progression of chronic kidney disease in patients are provided by the present invention.

Particularly, it is provided herein prognostic methods and kits allowing prediction of the fast progression of CKD and thus risk of progression to end stage renal disease in patients.

According to the present invention, highly reliable sets of urinary biological markers that are indicative of an increased risk of fast progression of chronic kidney disease have been identified.

Thus, an object of the present invention consists of an in vitro method for the prediction of fast progression of chronic kidney disease in a subject, comprising the steps of evaluating the expression of one or more biomarkers in a biological sample obtained from said subject, wherein said one or more biomarkers are selected from the group consisting of epidermal growth factor (EGF), monocyte chemoattractant protein 1 (MCP1), transforming growth factor alpha (TGF-α), Growth and Differentiation Factor 15 (GDF15), neutrophil gelatinase-associated lipocalin (NGAL), Cystatin C, Fatty Acid Binding Protein (FABP), Fibronectin, Kidney Injury Molecule 1 (KIM1), Osteopontin, Tissue Inhibitor of Mettaloprotease 1 (TIMP1), Uromodulin Interleukin-6 (IL6), Leukemia Inhibitory Factor (LIF), Matrix Metallopeptidase 9 (MMP9) and Vascular Endothelial Growth Factor A (VEGFA).

In specific embodiments, the expression of 2, 3, 4 or 5 of said biomarkers listed above is evaluated.

Said one or more biomarkers of the prediction method according to the invention are more particularly selected from the group consisting of EGF, MCP1 and TGF-α.

In specific embodiments, the prediction method of the invention comprises evaluating at least the expressions of EGF, MCP1 and TGF-α for example, their protein expression, and optionally, of NGAL.

As it is shown in the examples below, when comparing the expression values of candidate biomarkers in urine samples between slow progressor and fast progressor of CKD, the inventors have identified specific biomarkers and their combinations with statistically different expression in fast progressor vs slow progressor or healthy subjects, such biomarkers are called hereafter the "predictive biomarkers" and listed in Table 1 below.

Certain Definitions

The term "patient" or "subject" which is used herein interchangeably refers to a human being, including for example a man or a woman that has or is suspected to have a chronic kidney disease or is at an early stage of CKD, or a subject at risk in developing chronic kidney disease considering the demographic risk factors of CKD.

The term "chronic kidney disease" or "CKD" is used herein interchangeably to refer to a condition defined as abnormalities of kidney structure or function, present for more than 3 months, with implications for health which can occur abruptly, and either resolve or become chronic (Clinical Practice Guideline for the Evaluation and Management of Chronic Kidney Disease Guidelines (KDIGO 2012). CKD is a general term for heterogeneous disorders affecting kidney structure and function with variable clinical presentation, in part related to cause, severity and the rate of progression (Kidney International Supplements (2013) 3, vii). In particular, definition and identification of CKD may be defined with the following criteria:
1. For individuals at higher risk of progression, and/or where measurement will impact therapeutic decisions
2. Recognize that small fluctuations in GFR are common and are not necessarily indicative of progression.
3. Define CKD progression based on one of more of the following (Not Graded): a. Decline in GFR category (Z90 [G1], 60-89 [G2], 45-59 [G3a], 30-44 [G3b], 15-29 [G4], o15 [G5] ml/min/1.73 m2). A certain drop in eGFR is defined as a drop in GFR category accompanied by a 50% or greater drop in eGFR from baseline or End-Stage Renal Disease (ESRD, eGFR<15 ml/min/1.73 m2, Renal Replacement Therapy or death or composite of the above parameters.
b. Rapid progression is defined as a sustained decline in eGFR of more than −3.3% per year.
c. The confidence in assessing progression is increased with increasing number of serum creatinine measurements and duration of follow-up The term "biological sample" is intended to refer to biological fluids and isolates thereof isolated from a subject. It can include without limitation, blood sample, e.g., whole blood, plasma and serum sample, saliva or urine sample. In a particular embodiment, a biological sample is urine sample.

The term "prognosis" is used herein to refer to the prediction of the outcome of the patient as to whether their GFR falls at fast or slow rate.

As used herein, the term "prediction of fast progression" does not necessarily consist of an absolute response. It may allow to determine the probability (risk) of fast progression of chronic kidney disease in a subject, or, it may consist of a response allowing to determine an increased risk of fast progression in a subject compared to the average risk of fast progression of CKD in a population, rather than giving a precise probability for the risk.

In other words, a patient who is predicted to be a fast progressor according to the methods of the invention is a subject at increased risk of being a fast progressor. In certain embodiments, the prediction is expressed as a statistical value, including a P value, as calculated from the expression values obtained for each of the one or more biomarkers that have been evaluated.

The term "fast progression" particularly refers to an evolution of CKD as measured by the loss of more than 10% of the baseline measured glomerular filtration rate (mGFR) per year in a subject suffering from CKD also called herein "fast progressor". Fast progressors are more likely to progress onto end stage renal disease (ESRD), which stage is associated with a significant morbidity and mortality risk. Accordingly, in a specific embodiment of the methods of the invention, a subject predicted of fast progression, is a subject predicted to lose more than 10% of the baseline measured glomerular filtration rate (mGFR) per year, for example as measured from an initial measurement until a subsequent time around a year later. On the contrary, a "slow progressor" is a subject that is losing less than 10% of the baseline measured glomerular filtration rate (mGFR) per year.

As used herein, the term "early prediction" refers to a prediction carried out in a subject at an early stage of CKD, for example at stage 1 or 2, with GFR>60 ml/mn/1.73 m2 33, stage 3 or which even who has not yet been diagnosed as having CKD, for example according to albuminuria, proteinuria or creatinine concentration conventional diagnostic methods. The prognosis methods of the invention are particularly appropriate for early prediction of fast progression of CKD in a subject.

As used herein, the term "biological marker" or "biomarker" refers to an indicator of e.g. a pathological state of a patient, which can be detected in a biological sample of the patient. Biomarkers, include, but are not limited to, DNA, RNA, protein, carbohydrate, or glycolipid-based molecular markers.

The term "protein" is used interchangeably with the term "polypeptide" and in its broadest sense refers to a compound of two or more subunit amino acids. The subunits can be linked by peptide bonds.

The term "kit" as used herein refers to a collection of the aforementioned components which may be provided separately or within a single container. The container also comprises instructions for carrying out the method of the present disclosure. These instructions may be in the form of a manual or may be provided by a computer program code which is capable of carrying out the comparisons referred to in the methods of the present disclosure and to establish a diagnosis accordingly when implemented on a computer or a data processing device. The computer program code may be provided on a data storage medium or device such as an optical storage medium (e.g., a Compact Disc) or directly on a computer or data processing device.

The Predictive Biomarkers for Use in the Methods of the Invention

The predictive biomarkers are described hereafter by their acronyms, full name and UniprotKB/Swiss-Prot nomenclature and SEQ ID NOs.

differences in the expression values compared to the respective control values is indicative that the subject is at increased risk of fast progression.

Expression of the biomarkers can be quantified by determining gene or protein expression of the predictive biomarkers in the biological sample of a subject, for example serum or urine sample. The quantification may be relative (by comparing the amount of a biomarker to a control with known amount of biomarker for example and detecting "higher" or "lower" amount compared to that control) or more precise, at least to determine the specific amount relative to a known control amount.

In one specific embodiment, the expression of the biomarkers can be quantified by examining protein expression of at least one or more of the predictive biomarkers in the biological sample, for example urine sample, of a subject. In specific embodiments, the protein expressions of at least EGF, MCP1 and TGF-α and optionally, NGAL are quantified in the biological sample of a subject, for example urine sample.

Various methods are known in the art for detecting protein expression levels in such biological samples, including various immunoassays methods. They include but are not limited to radioimmunoassays, ELISA (enzyme linked immunosorbent assays), "sandwich" immunoassays, immu-

TABLE 1

List of predictive biomarkers

| Biomarker | Full name | UniprotKB/Swiss-Prot[1] | SEQ ID NO: |
|---|---|---|---|
| EGF | Epidermal Growth Factor | P01133 | 1 |
| GDF15 | Growth and Differentiation Factor 15 | Q99988 | 2 |
| TGF-α | Transforming Growth Factor alpha | P01135 | 3 |
| MCP1 | Monocyte Chemoattractant Protein 1 | P13500 | 4 |
| FABP1 | Fatty Acid Binding Protein | P07148 | 5 |
| Cystatin C | Cystatin C | P01034 | 6 |
| Fibronectin | Fibronectin | P02751 | 7 |
| KIM1 | Kidney Injury Molecule 1 | Q96D42 | 8 |
| NGAL | Neutrophil Gelatinase Associated Lipocalin | P80188 | 9 |
| TIMP1 | Tissue Inhibitor of Metalloprotease 1 | P01033 | 10 |
| Uromodulin | Uromodulin | P07911 | 11 |
| VEGF-A | Vascular Endothelial Growth Factor A | P15692 | 12 |
| Osteopontin | Osteopontin | P10451 | 13 |
| IL6 | Interleukin 6 | P05231 | 14 |
| LIF | Leukemia Inhibitory Factor | P15018 | 15 |
| MMP9 | Matrix Metallopeptidase 9 (MMP9) | P14780 | 16 |

[1]Information available on Uniprot knowledgeabase, which is an online database.

In the present invention, when referring to the biomarkers, it particularly refers to the protein of said biomarker and/or its post-translational modifications.

The protein sequences of the corresponding biomarkers can be found on Uniprot knowledgebase according to the corresponding references as shown in Table 1, or SEQ ID NOs 1-16. Of course, any natural variations of said protein sequences are included in the definition of said biomarkers for use in the present invention.

Quantifying the Expression of a Predictive Biomarker

The prediction method of the invention comprises a step of evaluating the expression of one or more of the predictive biomarkers in a biological sample.

As used herein, the term "evaluating" typically include the steps of (a) quantifying the expression of each of the selected predictive biomarkers in a biological sample obtained from said subject to obtain expression values, and (b) comparing the obtained expression values of said predictive biomarkers to corresponding control values, wherein noradiometric assays, in situ immunoassays (using e.g., colloidal gold, enzyme or radioisotope labels), western blot analysis, immunoprecipitation assays, immunofluorescent assays, flow cytometry, immunohistochemistry, confocal microscopy, enzymatic assays, surface plasmon resonance and PAGE-SDS.

Determining the protein level involves for example measuring the amount of any immunospecific binding that occurs between an antibody that selectively recognizes and binds to the polypeptide of the biomarker in a sample obtained from a patient. These assays may also include direct binding of labelled antibody to a target biomarker.

Sandwich assays are among the most useful and commonly used assays. A number of variations of the sandwich assay technique exist, and all are intended to be encompassed by the present invention. Briefly, in a typical forward assay, an unlabeled antibody is immobilized on a solid substrate, and the sample to be tested brought into contact with the bound molecule. After a suitable period of incubation, for a period of time sufficient to allow formation of an antibody-antigen complex, a second antibody specific to the antigen, but labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface.

The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40[deg.]C such as between 25[deg.] C and 32[deg.] C inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the predictive biomarkers in the sample and then exposing the immobilized biomarkers to specific antibody which may or may not be labeled with a reporter molecule. Depending on the amount of biomarker target and the strength of the reporter molecule signal, a bound biomarker target may be detectable by direct labelling with the antibody. Alternatively, a second labeled antibody, specific to the first antibody is exposed to the target-first antibody complex to form a target-first antibody-second antibody tertiary complex. The complex is detected by the signal emitted by the reporter molecule.

By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay or ELISA assay, an enzyme may typically be conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

In specific embodiment of the prediction method of the invention, the quantifying step thus allows to obtain an "expression value" for each biomarker tested in the biological sample, for use in the comparing step.

For ease of use in the comparing step, said expression value may consist of a normalized (relative) value which is obtained after comparison of the absolute expression level value with a reference value, said reference value consisting for example of the expression level value of reference proteins in the biological sample.

For example, in a specific embodiment, creatinine level may be used for adjusting the expression values to normalized expression values. Usually, creatinine can be determined by enzymatic or colorimetric test systems in urine.

Comparing Expression Value of Each Biomarker to Corresponding Control Values

The methods of the invention is based on quantifying the expression of one or more predictive biomarkers in a biological sample of a subject, as described above, and comparing each expression value of said biomarkers to corresponding control values.

The term "comparing" as used herein refers to a comparison of corresponding parameters or values, e.g. an absolute level value is compared to an absolute control level value which a concentration is compared to a control concentration and normalised value is compared to corresponding control normalised value.

As used herein, the term "control values" refers to expression values of the biomarkers in control subject or a group of control subjects, which allows assessing whether an individual is predicted of CKD fast progression.

According to some embodiments, the control value is determined based on biomarker expression from a control subject or a group of control subjects which has been characterized as fast progressor, slow progressor or as healthy subject.

The control value applicable for a specific subject may vary depending on various physiological parameters such as age, gender, or subpopulation, as well as on the test format, the sample and the ligand used for the quantification of the biomarker referred to herein. These factors and ways to take them into account when determining the control values are generally known in the field. In some embodiments, control values can be calculated for a cohort of subjects as specified in the Examples, based on the average or mean or median values for a biomarker by applying standard statistical methods.

Accordingly a control value to be used for the aforementioned method of the present invention (i.e. a threshold which allows for identifying an individual at higher risk of fast progression) may be the mean/median expression value (or normalized (relative) mean/median value) of a biomarker protein expression as quantified in a group of control subjects.

Examples of such normalized median values for each predictive biomarkers in men and women are given in the Examples below at Table 3 (the values have been adjusted to normalized value with urine creatinine concentration).

Said control value can also be determined by routine experimentation depending on the quantification methods and the predictive biomarkers that will be used for the methods of the invention.

For example, said control value corresponds to the expression (optionally normalized) mean/median value observed for slow progressor group of patients, and a patient is predicted to be a fast progressor when the expression (optionally normalized) value is statistically different from the control value, for example increased as compared to the control value, or decreased as compared to a control value.

Alternatively, said control value corresponds to the expression level value observed for fast progressor patients, and a patient is predicted to be a fast progressor when the expression level value is statistically not different from the control value.

For example, in a specific prediction method of the invention, the evaluating step include (a) quantifying the expression of one or more of the selected biomarkers in a biological sample obtained from said subject to obtain an expression value for each biomarker, and (b) comparing said expression value of each biomarker obtained at step (a) to a corresponding control value, wherein an expression value of EGF below a control value and/or an expression value of MCP1 above a control value, and/or an expression value of TGF-α above a control value, and/or an expression value of NGAL above a control value, indicates that the subject is at increased risk of fast progression of CKD.

The comparison referred to in step (b) of the methods of the invention may be carried out manually or computer assisted.

For a computer-assisted comparison, the expression values may be compared to control values which are stored in a database by a computer program. The computer program may further evaluate the result of the comparison, i.e. automatically provide the desired assessment in a suitable output format.

As it is shown in the examples and more specifically in Table 5 of the Examples below, a combination of 2, 3, 4, or 5 of the predictive biomarkers according to the invention can be statistically relevant for predicting fast progression of CKD for a patient.

Any combination of two, three, four, five or more of the predictive biomarkers of the invention is encompassed by the methods of the invention.

The comparing step may not necessarily include a separate comparison of the expression values of each biomarker with their corresponding control values. In specific embodiments, a multi-biomarker score value can be obtained by combining together the expression values or their normalized values and compared to a corresponding multibiomarker score control value.

In a particular embodiment, the expression values are obtained at least for the three following biomarkers in a patient: epidermal growth factor (EGF), monocyte chemoattractant protein 1 (MCP1), and transforming growth factor alpha (TGF-α) and, optionally, of NGAL.

To improve statistical prediction of the methods according to the invention, one can further include the albuminuria, proteinuria, plasma or serum creatinine concentration and/or demographic risk factors for chronic kidney disease progression.

As used herein, said demographic risk factors include age, body mass index, mean arterial pressure, gender, Black/African ethnicity, diabetes, history of cardiovascular diseases, smoker, satus, the non-use of angiotensin pathway blockade, history of urinary infections, haematuria, familial history of kidney disease.

In a specific embodiment, the invention relates to a method for the prediction of fast progression of chronic kidney disease in a subject, comprising evaluating at least the expressions of EGF, MCP1 and TGF-α, and, optionally, NGAL, and wherein albuminuria or proteinuria is further determined from said subject. Albuminuria or proteinuria may be determined from the same biological sample or in a different biological sample according to well known methods in the art.

In specific embodiments, the prediction methods include evaluating the expressions of at least epidermal growth factor (EGF), monocyte chemoattractant protein 1 (MCP1), and transforming growth factor alpha (TGF-α) and at least one or more of the following biomarkers: GDF15, FABP1, Cystatin C, Fibronectin, KIM1, NGAL, TIMP1, Uromodulin, Osteopontin, IL6, MMP9, LIF and VEGF-A.

In specific embodiments, the prediction methods include evaluating the expression in urine sample of the specific biomarker combination of EGF, TGF-α and MCP1.

In other specific embodiments, the prediction methods include evaluating the expression in urine sample of the specific biomarker combination of EGF, TGF-α, MCP1 and NGAL.

In other specific embodiments, the prediction methods include evaluating the expression in urine sample of the specific biomarker combination of EGF, TGF-α, MCP1 and NGAL.

In other specific embodiments, the prediction methods include evaluating the expression in urine sample of the specific biomarker combination of EGF, TGF-α, MCP1, and FABP1.

In other specific embodiments, the prediction methods include evaluating the expression in urine sample of the specific biomarker combination of EGF, TGF-α, MCP1 and Cystatin C.

In other specific embodiments, the prediction methods include evaluating the expression in urine sample of the specific biomarker combination of EGF, TGF-α, MCP1 and Fibronectin.

In other specific embodiments, the prediction methods include evaluating the expression in urine sample of the specific biomarker combination of EGF, TGF-α, MCP1 and KIM1.

In other specific embodiments, the prediction methods include evaluating the expression in urine sample of the specific biomarker combination of EGF, TGF-α and TIMP1.

In other specific embodiments combined with the above specific embodiments, the prediction methods also include evaluating albumin in urine sample, either together with the other predictive biomarkers (from the same biological sample) or separately (from different sample).

Assaying for Biomarker Expression and the Treatment for CKD

The invention further relates to patient stratification methods. In particular, patient identified at increased risk of fast progression of CKD may be selected according to the methods of the invention for a therapeutic treatment of CKD. Accordingly, the invention further includes a method comprising (i) identifying whether a patient is at increased risk of fast progression of CKD according to the above defined prediction methods, and, (ii) treating said fast progressor patient identified at step (i) with a suitable therapeutic agent for treating CKD.

As used herein, the term "treating" or "treatment" refers to measures, wherein the object is to prevent or slow down (lessen) the targeted pathologic condition or disorder or slow down or relieve one or more of the symptoms of the disorder. In a specific embodiment, a subject is "successfully treated" for chronic kidney disease if, after receiving a therapeutic agent, the patient shows observable and/or measurable decrease or change from baseline in and/or measurable rate of change from baseline over time (e.g. over 3 months [12 weeks], or 6 months [24 weeks], or 9 months [36 weeks], or 12 months [1 year, 52 weeks] in one or more of the following: mGFR, percentage loss of mGFR in 1 year, eGFR, percentage of loss in eGFR.

Therapeutic agents for treating fast progressors of chronic kidney disease according to the above methods, may include without limitation (i) an angiotensin converting enzyme inhibitor (ACEi) such as, Captopril (Capoten), Zofenopril, Enalapril (Vasotec/Renitec), Ramipril (Altace/Prilace/Ramace/Ramiwin/Triatec/Tritace), Quinapril (Accupril), Perindopril (Coversyl/Aceon/Perindo), Lisinopril (Listril/Lopril/Novatec/Prinivil/Zestril), Benazepril (Lotensin), Imidapril (Tanatril), Trandolapril (Mavik/Odrik/Gopten), Cilazapril (Inhibace) and Phosphonate-containing agents such as Fosinopril (Fositen/Monopril) or (ii) an angiotensin receptor blocker (ARB) such as Losartan (Cozaar), Candesartan (atacand), valsartan (Diovan), Irbesartan (Avapro), Telmisartan (Micardis), Eprosartan (Teveten), Olmesartan (Benicar/Olmetes) and Azilsartan (edarbi).

Administration of a suitable therapeutic agent for treating chronic kidney disease to said patient can be effected in one dose, continuously or intermittently throughout the course of treatment.

Methods of determining the most effective means and dosage of administration of a treatment are well known to those of skill in the art and will vary with the composition used for therapy, the purpose of the therapy, and the subject being treated. Single or multiple administrations can be carried out with the dose level and pattern being selected by the treating physician. Suitable dosage formulations and methods of administering the agents may be empirically adjusted.

If a patient is predicted to be a slow progressor, alternative therapies may be preferred. Prior to administering suitable therapeutic agents, further diagnosis methods may be applied to further validate the risk of fast progression in said patient.

Another aspect of the invention relates to an in vitro method for monitoring the efficacy of a treatment for treating chronic kidney disease in a patient, comprising evaluating expression of one or more of the predictive biomarkers as defined in Table 1 above.

In particular, said predictive biomarkers which can be used in the monitoring methods of the invention are selected from the group consisting of epidermal growth factor (EGF), monocyte chemoattractant protein 1 (MCP1), and transforming growth factor alpha (TGF-$\alpha$), and, optionally, NGAL.

In such monitoring methods, the evaluating step is carried out essentially the same as described above for the prediction method of the invention, except that the subject is a subject in need of a treatment for CKD, and the predictive biomarkers are now used as surrogate markers, i.e. as predictors of the disease stage or of mGFR parameter. The evaluating step can be performed for example prior to treatment, and during or at the end of the treatment and evolution/change of expression levels of each biomarker is indicative of a good or poor response to the treatment.

Such methods can be used for example to monitor the efficacy of regulatory approved treatments of CKD in patients, and/or adjust dosage or length of the treatment. Alternatively, such methods can be used to monitor the efficacy of candidate treatments in clinical studies.

Kits of the Invention

The invention further relates to kits for the prediction or monitoring methods of the invention.

In particular, one object of the invention consists of a kit for the prediction of fast progression of chronic kidney disease in a subject (e.g. in a biological sample, more particularly in a urine sample of the subject), said kit comprising means for quantifying protein expression of at least the following biomarkers: epidermal growth factor (EGF), monocyte chemoattractant protein 1 (MCP1), and transforming growth factor alpha (TGF-$\alpha$).

Another object of the present invention consists of a kit for monitoring the efficacy of a treatment for treating chronic kidney disease, said monitoring kit comprising means for quantifying protein expression of at least the following predictive biomarkers: epidermal growth factor (EGF), monocyte chemoattractant protein 1 (MCP1), and transforming growth factor alpha (TGF-$\alpha$).

In certain embodiments of said kits, they comprise means for detecting and/or quantifying 2, 3, or all of the following predictive biomarkers: EGF, MCP1, TGF-$\alpha$ and NGAL.

The monitoring or prediction kit of the invention may thus include a plurality of reagents, each of which is capable of binding specifically with a protein of one of the predictive biomarkers. Suitable reagents for binding specifically with a protein biomarker include, without limitation, antibodies.

As used herein the term "antibody" is used in a broader sense and includes whole antibodies and any antigen binding fragments or derivatives (i.e., "antigen-binding portion"). It may specifically cover monoclonal antibodies, polyclonal antibodies, multi-specific antibodies, single chains thereof. Antigen binding fragments also include, Fab, Fab', (Fab')2 and their derivatives including a combination of VH and VL fragments, or Fv antibodies, Fv being the minimum antibody fragment which contains a complete antigen-recognition and -binding site. It further includes, chimeric, humanized or human antibodies.

A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

An "isolated antibody", as used herein, refers to an antibody that is substantially free of other antibodies having different antigenic specificities. Moreover, an isolated antibody may be substantially free of other cellular material and/or chemicals.

The terms "monoclonal antibody" and "monoclonal antibody composition" as used herein refer to a preparation of antibody molecules of single molecular composition. A monoclonal antibody composition displays a single binding specificity and affinity for a particular epitope.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM, IgE, IgG such as IgG1 or IgG4) that is provided by the heavy chain constant region genes.

The phrases "an antibody recognizing an antigen" and "an antibody specific for an antigen" and "an antibody reacting specifically to an antigen" are used interchangeably herein with the term "an antibody which binds specifically to an antigen".

As used herein, an antibody or a protein that "specifically binds to a protein biomarker" is intended to refer to an antibody or protein that binds to said protein biomarker with a KD of 100 nM or less, 10 nM or less, 1 nM or less, 100 pM or less, or 10 pM or less.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction.

The term "KD", as used herein, is intended to refer to the dissociation constant, which is obtained from the ratio of Kd to Ka (i.e. Kd/Ka) and is expressed as a molar concentration (M). KD values for antibodies can be determined using methods well established in the art. A method for determining the KD of an antibody is by using surface plasmon resonance, or using a biosensor system such as a Biacore® system.

The prediction or monitoring kit of the invention may further include antibodies for detecting or quantifying capture antibodies in an immunoassay.

For example, the monitoring or prediction kit of the invention may include second antibodies for detecting or quantifying biomarker protein/antibodies complex in an immunoassay. Accordingly, the monitoring or prediction kit comprises (i) a set of unlabeled antibodies which, each, bind to one or more predictive biomarkers particularly selected from the group consisting of: epidermal growth factor (EGF), monocyte chemoattractant protein 1 (MCP1), and transforming growth factor alpha (TGF-α), and/or (ii) a set of labelled antibodies which, each, bind to one or more predictive biomarkers particularly selected from the group consisting of: epidermal growth factor (EGF), monocyte chemoattractant protein 1 (MCP1), and transforming growth factor alpha (TGF-α), Alternatively, the kit may comprise:

(i) a first set of unlabeled antibodies which, each, bind to one or more predictive biomarkers particularly selected from the group consisting of: epidermal growth factor (EGF), monocyte chemoattractant protein 1 (MCP1), and transforming growth factor alpha (TGF-α), (ii) a second set of labelled antibodies which bind to said first set of labelled antibodies to form a biomarker/first antibody/second antibody complex.

The labelled antibody as used in the kits of the invention may typically comprise an antibody conjugated to a reporter molecule. In specific embodiments of the kits as above defined, the labelled antibody is an antibody conjugated to an enzyme, for example an enzyme for ELISA assay, such as horseradish peroxidase, glucose oxidase, -galactosidase, and alkaline phosphatase, amongst others. The kit may further include corresponding substrates for such enzymes.

Alternatively, the labelled antibody is an antibody conjugated with fluorescent compounds, for example, fluorescin or rhodamine.

The kits as defined above may further include antibodies (unlabelled and/or labelled) which bind to NGAL.

Optionally, said monitoring or prediction kit of the invention may further comprise means for detecting and/or quantifying one or more reference (control) marker, e.g. markers corresponding to ubiquitously expressed proteins, or other biomarker of CKD, such as creatinine or albumin.

In a specific embodiment, the kit of the invention, for use in an immunoassay, comprises at least:
(i) antibodies specific of epidermal growth factor (EGF);
(ii) antibodies specific of monocyte chemoattractant protein 1 (MCP1); and,
(iii) antibodies specific of transforming growth factor alpha (TGF-α).

Said antibodies for use in the kits of the invention may be immobilized on a support, for example a glass or a polymer, more particularly, polymers selected among cellulose, polyacrylamide, nylon, polystyrene, polyvinyl chloride or polypropylene. The solid supports may be in the form of tubes, beads, discs of microplates, or any other surface suitable for conducting an immunoassay.

The prediction kit and the monitoring kit of the invention may optionally comprise additional components useful for performing the methods of the invention. By way of example, the kits may comprise fluids (e.g. buffers) suitable for binding an antibody with a protein with which it specifically binds, one or more sample compartments, washing the reactants to remove unspecific binding, and instructional materials which describe performance of the prediction or monitoring methods of the invention and the like.

Another aspect of the invention provides for a device adapted for carrying out the prediction or monitoring methods of the invention, said device comprising:

a) an analyzing unit comprising a combination of detection means which specifically bind to the biomarkers (e.g. antibodies as described above in the kits), the analyzing unit being adapted for contacting, in vitro, the sample from the subject with the detection agent;

b) an evaluation unit including a computing device having a database and a computer-implemented algorithm on the database, the computer-implemented algorithm when executed by the computing device determines an amount of one or more of the predictive biomarkers in the sample, e.g., urine sample, from the subject, and compares the determined amount of said one or more predictive biomarker with corresponding control values and provides a prediction of fast progression if the amount of said one or more predictive biomarker is significantly different, for example significantly greater or lower than a control value.

In one specific embodiment, the database further includes the control values for each of the predictive biomarkers.

EXAMPLES

Methods
NephroTest Cohort Protocol

Patients were recruited from the NephroTest cohort that includes 1825 patients with mGFRs with plasma and/or urine samples to date since its commencement in 2000. The NephroTest cohort consists of patients from three large nephrology centres in Paris: Hôpital Européen Georges Pompidou, Hôpital Bichat and Hôpital Tenon. Inclusion criteria to the cohort were consenting adult patients with any stage of CKD. Exclusion criteria were patients already on any form of renal replacement therapy and pregnant patients. The urine collection biobank in the protocol commenced in 2009. We analysed data from 229 patients in whom there were stored urine collections and 2 or more concurrent mGFRs over time in order to assess disease progression. The median follow-up time for these patients in the cohort from the time of the first urine collection was 21.6 (IQR, 13.6-24.7) months, and 57 of these patients had up to 3 sequential mGFRs from time of first urine collection. First urine collection from these 229 patients was analysed. The clinical and biological data collected from patients is as previously described[31].

The NephroTest cohort study is approved and sponsored by the French Institute of Health and Medical Research (INSERM). All patients provided written informed consent for long-term handling of frozen biological samples and of pre-specified clinical and biologic data for research use. The study was conducted in accordance with good clinical practice guidelines.

Technical Methods (Urinary Biomarkers Measurements)

Urine was collected and stored at −80° C. after a maximal 4 hour period at 4° C. Urine supernatant was stored after initial centrifugation at 1000 g for 10 minutes in a tube containing antiprotease (cOmplete; Protease Inhibitor Cocktail Tablets, Roche applied Science).

The biomarkers ELISA kits used were R&D systems for cystatin C, epidermal growth factor (EGF), growth and differentiation factor 15 (GDF15), interleukin 6 (IL6), monocyte chemoattractant protein 1 (MCP1), matrix metalloprotease 9 (MMP9), osteopontin, kidney injury molecule 1 (KIM1), tissue inhibitor of metalloprotease 1 (TIMP1), Transforming growth factor alpha (TGF-α), and vascular endothelial growth factor A (VEGFA); eBioscience for Fibronectin and leukaemia inhibitory factor (LIF); Bioporto for neutrophil gelatinase associated lipocain (NGAL); CMIc for fatty acid binding protein 1 (FABP1), and MdBiproduct for uromodulin. All ELISA kits were formally validated following rigorous criteria prior to utilisation [unpublished data].

Urine creatinine was measured in the biochemistry laboratory at Hôpital Necker Enfants-Malades using the enzymatic method standardised for isotope dilution mass spectrometry (IDMS). Urinary protein and albumin were measured the standard methods in the hospital laboratory.

Measurement and Definition of CKD Progression

As reported elsewhere, all patients in NephroTest cohort had GFRs measured by chromium-51 labelled ethylenediaminetetraacetic (EDTA) acid clearance.[31] Individual slopes in mL/min/year were estimated using ordinary linear regression. We then calculated relative mGFR slopes in % per year and categorized patients into two groups of rate of decline in baseline mGFR: ≤10 vs.>10% per year. Estimated GFRs (eGFRs) were also calculated using the Modification of the in Renal Disease formula[32] and then the values obtained were unadjusted for body surface area (BSA) to allow for a direct comparison of the eGFR with the corresponding mGFR values.

Statistical Analysis

Clinical and laboratory data are expressed as percentages, means (±standard deviation, SD) or median (interquartile range, IQR), as appropriate. Biomarkers, albuminuria and proteinuria to creatinine ratios, have skewed distributions and thus were subsequently logarithmically transformed. NGAL and cystatin C required two sequential logarithmic transformations to approach a normal distribution. Log-transformed values were then standardized to a mean of 0 and SD of 1, using gender specific means and SDs i.e. (measured value−mean) divided by the SD, to account for gender-related differences.

We compared baseline clinical and laboratory data and CKD risk factors between slow and fast progressors (using the cut off of 10% decline per year in mGFR). Continuous variables were compared with the Wilcoxon test and categorical variables with the chi-squared or Fisher's exact test. Gender differences regarding biomarkers and mGFR slopes were similarly tested. Association between biomarkers and concurrently mGFR at first visit and between biomarkers and % change in mGFR were first assessed using Pearsons correlation. Logistic regression was then used to estimate the crude and adjusted odds ratios (OR) of fast progression for each of the biomarkers. OR were sequentially adjusted for mean mGFR over time and baseline covariates: age, gender, black African origin, BMI, mean blood pressure, diabetes mellitus, history of cardiovascular disease, smoking, renin angiotensin aldosterone system (RAAS) blockade such as angiotensin converting enzyme inhibitor (ACEI) or angiotensin receptor blocker (ARB) treatment, and finally for albuminuria. The mean mGFR instead of the baseline mGFR was used as a covariate in the analysis to reduce the phenomenon of 'regression to the mean[3].

In order to determine the best combination of biomarkers to predict CKD progression, several models of logistic regression combining biomarkers and albuminuria were built apriori principally from pathophysiological hypotheses. Biomarkers associated individually with CKD progression were favoured in the model but we avoided adding together biomarkers correlating with each other or with albuminuria at more than 0.55 (Pearson correlation). These models were additionally adjusted for mean GFR and other significantly associated factors such as centre of recruitment and diabetes to limit the number of covariates. The six models constructed as such, were compared to a nested minimal model with only albuminuria and the same adjustment covariates but without the biomarkers. We calculated the area under the receiver operating characteristic (ROC) curve (AUC), the likelihood ratio test (LRT), the scale brier score (SBS), and the integrated discrimination index (IDI) to assess performance of theses predictive models for CKD progression. The improvement in the predictive value was estimated by comparing AUC of these models with the minimal reference model.

Statistical analyses were performed with SAS 9.2 (SAS Institute Inc., Cary, NC USA), R 2.3 (R Foundation for Statistical Computing, Vienna, Austria, 2014) and prism graphpad 5.0 for the animal data.

Results

Patient Characterisation and CKD Progression

We analysed in 229 patients with repeated mGFRs and concurrent urine collections. There were 152 (66.4%) men and the mean age at baseline (i.e. at the time at which first urine collection was performed) was 60.8±13.3 years. The median baseline mGFR was 38.3 (IQR, 26.4-49.6) ml/min. The median mGFR at last visit after a median follow up time of 21.6 (IQR, 13.6-24.7) months was 34.7 (IQR, 24.7-47.5) ml/min. The change in mGFR was −1.46 (IQR, −4.28, 1.08) ml/min/year equivalent to −4.0 (IQR, −12, 2.7) % per year from baseline (negative values represent a loss). 68 (30%) patients were defined as 'fast progressors' (loss of greater than 10% in their mGFR per year). The baseline characteristics in the slow and fast progressors are shown in Table 2. Albuminuria was significantly higher in fast progressors and diabetes was more frequent. Although a majority of the patients (89%) were on ACEI or ARB treatment, a higher proportion of the fast-progressors were on treatment (96% vs. 86%, p<0.04). Median mGFR during follow-up was as expected, lower in fast than in slow progressors (median IQR: 29.3(20.0, 37.5) vs. 40.9(30.1, 52.3) ml/min, p<0.0001), and the baseline mGFR was slightly lower in the fast progressors (p=0.06). Importantly, the number of mGFR measurements used to estimate progression rate was not significantly different between the two groups (more than 2 visits for 47% vs. 38%, p=0.2).

TABLE 2

Baseline characteristics of NephroTest patients.

| | All | Slow progressors | Fast Progressors | p-value |
|---|---|---|---|---|
| N | 229 | 161 | 68 | |
| Age, years | 60.8 ± 13.3 | 60.3 ± 13.3 | 62.0 ± 13.4 | 0.4 |
| Men | 66% (152) | 66% (106) | 68% (46) | 0.8 |
| Black African | 10% (23) | 12% (19) | 6% (4) | 0.2 |
| Diabetes | 25% (57) | 21% (34) | 34% (23) | 0.04 |
| Follow up (months) | 21.5 (13.4, 24.6) | 23.0 (14.3, 24.9) | 17.6 (12.8, 24.1) | 0.07 |
| First mGFR (mls/min) | 38.3 (26.3, 49.6) | 39.9 (28.9, 50.4) | 34.9 (24.4, 44.0) | 0.06 |
| Mean Blood Pressure | 92 ± 13 | 92 ± 12 | 92 ± 14 | 0.9 |
| Elevated blood pressure (>140/90) | 26% (57) | 24% (38) | 28% (19) | 0.5 |
| ACEI or ARB | 89% (202) | 86% (137) | 96% (65) | 0.04 |
| Body Mass Index, kg/m$^2$ | 27.2 ± 5.9 | 27.0 ± 5.8 | 27.7 ± 6.1 | 0.3 |
| History of Cardiovascular Event | 17% (38) | 16% (25) | 19% (13) | 0.5 |
| Previous/Current smokers | 38% (87)/ 10% (22) | 35% (57)/ 11% (17) | 44% (30)/ 7% (5) | 0.4 |
| Type of Nephropathy | | | | |
| PKD | 7% (16) | 4% (7) | 13% (9) | 0.2 |
| Diabetic nephropathy | 8% (19) | 7% (12) | 10% (7) | |
| Glomerular disease | 16% (37) | 16% (26) | 16% (11) | |
| Vascular | 25% (57) | 26% (42) | 22% (15) | |
| Chronic Interstitial Disease | 17% (39) | 19% (30) | 13% (9) | |
| Unknown | 27% (61) | 27% (44) | 25% (17) | |
| Proteinuria (mg/mmol) | 0.2 (0.1, 0.5) | 0.1 (0.1, 0.4) | 0.3 (0.1, 0.7) | 0.0002 |
| Albuminuria (mg/mmol) | 77 (17,291) | 52 (12,228) | 189 (40,485) | 0.0001 |

ACEI: Angiotensin converting enzyme inhibitor; ARB: angiotensin receptor blocker; mGFR: measured glomerular filtration rate by chromium labelled EDTA; PKD: polycystic kidney disease.
Data are expressed as mean ± standard deviation (SD), median (interquartile range (IQR)) or percent % (number of patients (n))

Biomarker Characterization and Gender Distribution

In biomarkers, TIMP1, VEGFA, KIM1, and osteopontin, where only less than 5% of the patients had values falling below the lower limit of detection (LLD), half of the value for the LLD was imputed for each patient (no more than 5 values were imputed in each case). In biomarkers (proteinuria, albuminuria, and FABP1) were 5 to 10% of the patients were affected, a random value between 0 and 1 multiplied by the LLD value was imputed. Finally, the biomarkers MMP9, IL6, and LIF, where more than 20% of the patients had values below the LLD, were described but not included in our subsequent analysis.

The biomarker distributions in the cohort are detailed in Table 3. The distributions varied by gender in five of the biomarkers (MMP9 and LIF not included). We found at baseline significantly higher levels of NGAL, TGF-α, and uromodulin in women. Conversely, we also observed higher levels of TIMP1 and VEGFA in men. There was no difference in baseline mGFR normalised for body surface area (BSA) between men and women (36.8 vs. 34.6 mls/min/1.73 $m^2$, p=0.3). The proportion of 'fast progressor' men was not significantly different from the 'slow progressor' men (68% vs. 66%, p=0.8, Table 1).

of being in a 'fast progressor' status was, as expected, increased by albuminuria and/or proteinuria. It was also increased by elevations in levels of cystatin C, FABP1, fibronectin, GDF15, KIM1, MCP1, NGAL, TIMP1, TGF-α and VEGFA. The risk was however reduced by increases in EGF. When traditional risk factors for CKD progression were added to the regression model, the risks were attenuated and there was further attenuation by adjusting for albuminuria (Table 4). Fibronectin, MCP1, TIMP1 and TGF-α however remained significantly associated with the risk after taking into account the role of all these factors. Interestingly, the effect size on progression was higher with TGF-α (OR 2.34) than with albuminuria (OR 1.72).

TABLE 3

Distribution of urinary biomarkers by gender

|  | N | All median [IQR] | Men median [IQR] | Women median [IQR] | p-value |
|---|---|---|---|---|---|
| Cystatin C, ng/mmol | 229 | 4.99 [3.28-17.22] | 4.94 [3.17-17.71] | 5.31 [3.45-14.2] | 0.5 |
| EGF, µg/mmol | 229 | 0.60 [0.38-0.93] | 0.56 [0.37-0.86] | 0.64 [0.40-1.18] | 0.06 |
| FABP1, µg/mmol | 216 | 1.58 [0.59-5.12] | 1.79 [0.58-5.57] | 1.43 [0.66-3.75] | 0.6 |
| Fibronectin, µg/mmol | 229 | 61.0 [44.7-92.3] | 59.5 [42.4-91.8] | 65.7 [48.5-92.2] | 0.2 |
| GDF15, µg/mmol | 229 | 0.75 [0.49-1.16] | 0.79 [0.53-1.19] | 0.62 [0.44-1.12] | 0.09 |
| IL6, ng/mmol | 176 | 0.43 [0.17-0.82] | 0.39 [0.16-0.84] | 0.48 [0.17-0.81] | 0.5 |
| KIM1, µg/mmol | 222 | 0.07 [0.04-0.12] | 0.07 [0.04-0.12] | 0.07 [0.04-0.12] | 0.5 |
| LIF, ng/mmol | 154 | 2.64 [1.62-4.55] | 2.41 [1.48-3.82] | 3.47 [2.01-5.47] | 0.02 |
| MCP1, ng/mmol | 229 | 24.0 [15.5-39.4] | 22.3 [15.3-40.1] | 26.3 [15.9-38.1] | 0.5 |
| MMP9, µg/mmol | 168 | 0.05 [0.01-0.26] | 0.03 [0.01-0.08] | 0.26 [0.05-0.90] | <0.0001 |
| NGAL, µg/mmol | 229 | 4.12 [2.19-10.81] | 2.98 [1.79-7.12] | 8.00 [3.28-18.34] | <0.0001 |
| Osteopontin, µg/mmol | 227 | 76.0 [45.8-107.1] | 74.7 [46.0-106] | 77.1 [36.7-109] | 0.99 |
| TIMP1, µg/mmol | 228 | 0.24 [0.13-0.47] | 0.31 [0.18-0.56] | 0.14 [0.08-0.25] | <0.0001 |
| TGF-α, ng/mmol | 229 | 0.38 [0.26-0.54] | 0.33 [0.24-0.48] | 0.44 [0.34-0.55] | 0.0003 |
| Uromodulin, mg/mmol | 227 | 1.58 [0.81-2.97] | 1.39 [0.74-2.91] | 2.09 [1.21-2.98] | 0.02 |
| VEGFA, ng/mmol | 227 | 10.2 [6.1-16.5] | 11.5 [6.8-19.4] | 8.7 [4.3-11.2] | <0.0001 |

Values given are adjusted for urine creatinine concentration.

N, number of patients; IQR, Interquartile range; min: minimum value recorded; max: maximum value recorded; EGF, Epidermal Growth Factor; FABP1, Fatty Acid Binding Protein 1; GDF15, Growth Differentiation Factor 15; IL6, Interleukin 6; KIM 1, Kidney Injury Molecule 1; LIF, Leukemia Inhibitory Factor; MMP9, Matrix Metalloprotease 9; MCP1, Monocyte Chemoattractant Protein 1; NGAL, Neutrophil Gelatinase Associated Lipocalin; TIMP 1, Tissue Inhibitor of Metalloprotease 1; TGF-α, Transforming Growth Factor alpha; VEGFA Vascular Endothelial Growth Factor A.

Individual Biomarker Association with CKD Progression

We observed no correlation between the baseline mGFR and the percent change in progression (r=−0.06, p=0.4). We then studied the association between urinary protein levels and the risk of being a 'fast progressor'. We initially studied each of the biomarkers individually and then subsequently sequentially adjusted each biomarker for known important risk factors for CKD progression including albuminuria in a multivariable logistic regression analysis (Table 4). The risk

TABLE 4 biomarker correlation with risk of 'fast progressor' (fall in mGFR >10% per year) status.

|  | Biomarker OR (95% CI) | +mean mGFR + *covariates OR (95% CI) | +albumin OR (95% CI) |
|---|---|---|---|
| Protein | 2.15(1.52, 3.03) | 1.87(1.24, 2.83) |  |
| Albumin | 2.08(1.48, 2.91) | 1.72(1.14, 2.58) |  |
| Cystatin C | 1.92(1.40, 2.65) | 1.72(1.13, 2.60) | 1.44(0.91, 2.28) |
| EGF | 0.62(0.46, 0.84) | 0.87(0.54, 1.38) | 0.96(0.59, 1.56) |
| FABP | 1.87(1.37, 2.54) | 1.53(1.06, 2.22) | 1.29(0.85, 1.96) |
| Fibronectin | 1.59(1.18, 2.15) | 1.60(1.13, 2.25) | 1.48(1.04, 2.11) |
| GDF15 | 1.60(1.17, 2.19) | 1.53(1.05, 2.22) | 1.40(0.95, 2.04) |
| KIM1 | 1.70(1.16, 2.51) | 1.54(1.01, 2.33) | 1.35(0.89, 2.06) |
| MCP1 | 2.10(1.51, 2.93) | 2.09(1.45, 3.01) | 1.95(1.35, 2.82) |
| NGAL | 1.50(1.12, 2.00) | 1.38(0.98, 1.95) | 1.25(0.87, 1.79) |
| Osteopontin | 1.09(0.80, 1.48) | 1.14(0.80, 1.62) | 1.10(0.79, 1.54) |
| TIMP1 | 2.02(1.45, 2.83) | 1.91(1.31, 2.78) | 1.72(1.15, 2.55) |
| TGF-α | 2.08(1.48, 2.92) | 2.34(1.57, 3.48) | 2.36(1.57, 3.54) |
| Uromodulin | 1.26(0.94, 1.69) | 1.29(0.91, 1.83) | 1.29(0.90, 1.84) |
| VEGFA | 1.82(1.31, 2.53) | 1.62(1.08, 2.41) | 1.46(0.97, 2.20) |

Abbreviations: mGFR, measured glomerular filtration rate; OR, odds ratio; CI, confidence interval; EGF, Epidermal Growth Factor; FABP1, Fatty Acid Binding Protein; GDF15, Growth and Differentiation Factor 15; KIM1, Kidney Injury Molecule 1; MCP1, Monocyte Chemoattractant Protein 1; NGAL, Neutrophil Gelatinase Associated Lipocalin; TIMP1, Tissue Inhibitor of Metalloprotease 1, TGF-α, Transforming Growth Factor alpha, VEGFA, Vascular Endothelial Growth Factor A.

Combining Urinary Biomarkers to Predict CKD Progression

Six different models combining 4 to 6 biomarkers were compared against the reference model with albuminuria (Table 5).

increased risk of being a 'fast progressor'. Analysing NGAL in tertiles instead of continuously revealed its complex relationship with progression (J-shaped pattern) after adjustment for other biomarkers (FIG. 3). For these reasons, model

TABLE 5

Biomarker combinations giving 6 different models associated with risk of fast progression:
*odds ratio (95% CI) of 'fast progressor' status (mGFR decline > 10% per year)·

|  | Model 0 | Model 1 | Model 2 | Model 3 | Model 4 | Model 5 | Model 6 |
|---|---|---|---|---|---|---|---|
| Albumin | 1.8 (1.23-2.62) | 1.7 (1.06-2.72) | 1.76 (1.08-2.86) | 1.55 (1.00-2.41) | 1.49 (0.96-2.30) | 1.68 (1.07-2.65) | 1.6 (1.03-2.49) |
| EGF |  | 0.54 (0.32-0.94) | 0.55 (0.33-0.95) | 0.59 (0.35-0.99) | 0.59 (0.35-1.01) | 0.51 (0.29-0.88) | 0.67 (0.40-1.10) |
| GDF15 |  | 0.94 (0.59-1.48) | 0.94 (0.60-1.48) | 0.85 (0.56-1.30) | 0.82 (0.54-1.24) | 0.99 (0.63-1.54) | 1.00 (0.67-1.49) |
| TGF-α |  | 2.53 (1.58-4.04) | 2.53 (1.59-4.03) | 2.4 (1.52-3.80) | 2.39 (1.53-3.74) | 2.9 (1.76-4.75) | 2.15 (1.39-3.32) |
| MCP1 |  | 1.96 (1.31-2.94) | 2.07 (1.36-3.14) | 1.99 (1.32-2.99) | 1.83 (1.19-2.81) | 2.22 (1.45-3.40) |  |
| FABP1 |  | 0.73 (0.43-1.24) |  |  |  |  |  |
| Cystatin C |  |  | 0.68 (0.39-1.20) |  |  |  |  |
| Fibronectin |  |  |  | 0.91 (0.58-1.38) |  |  |  |
| KIM1 |  |  |  |  | 1.20 (0.77-1.86) |  |  |
| NGAL |  |  |  |  |  | 0.54 (0.32-0.91) |  |
| TIMP1 |  |  | 0.98 (0.95-1.01) |  |  |  | 1.18 (0.74-1.90) |
| LRT (df) | Ref | 33.9 (5) | 34.6 (6) | 32.8 (5) | 33.3 (5) | 38.3 (5) | 21.6 (4) |
| p-value |  | <0.0001 | <0.0001 | <0.0001 | <0.0001 | <0.0001 | 0.0002 |
| AUC | 0.769 | 0.838 | 0.842 | 0.838 | 0.839 | 0.849 | 0.807 |
| SBS | 0.18 | 0.31 | 0.32 | 0.31 | 0.31 | 0.33 | 0.26 |
| IDI/rIDI | Ref | 13.3/74.1 | 13.5/75.5 | 12.8/71.7 | 12.8/71.8 | 15.2/84.2 | 8.1/45.5 |

Abbreviations: CI, confindence interval; SD, standard deviation; EGF, Epidermal Growth Factor; GDF15, Growth and Differentiation Factor 15; TGF-α, Transforming Growth Factor alpha; MCP1, Monocyte Chemoattractant Protein 1; FABP1, Fatty Acid Binding Protein; KIM1, Kidney Injury Molecule 1; NGAL, Neutrophil Gelatinase Associated Lipocalin; TIMP1, Tissue Inhibitor of Metalloprotease 1; LRT, likelihood ratio test; df, degrees of freedom; Ref, reference model; AUC, area under the curve; SBS, scale Brier score; IDI, integrated discrimination index; rIDI, relative IDI.
*odds ratios presented are per gender-specific SD unit increase (after log-transformation)· Models were adjusted for mean mGFR across visits, diabetes and recruitment centre.

Models were based on having biomarker reflecting different pathophysiological process and interbiomaker correlation within each model of <0.55. These models were adjusted only for mean mGFR and for significantly associated factors i.e. diabetes and the (NephroTest) recruitment centre. All models with biomarkers performed better than the reference model without the biomarkers (Table 5, likelihood ratio test), but the model containing EGF, GDF15, MCP1, NGAL, and TGF-α (model 5) was the best model according to all the performance criteria employed. In particular, biomarkers in model 5 significantly increased the area under the curve (AUC) of the receiver operating characteristic (ROC) curve from 0.77 to 0.85 (p=0.006) from the reference model (with albumin and without other biomarkers). Supporting these results, we also carried out a step-wise regression analysis with no a priori hypothesis as to functional role of biomarkers or interbiomarker correlations and interestingly obtained exactly the same combination of biomarkers.

Figure 1:
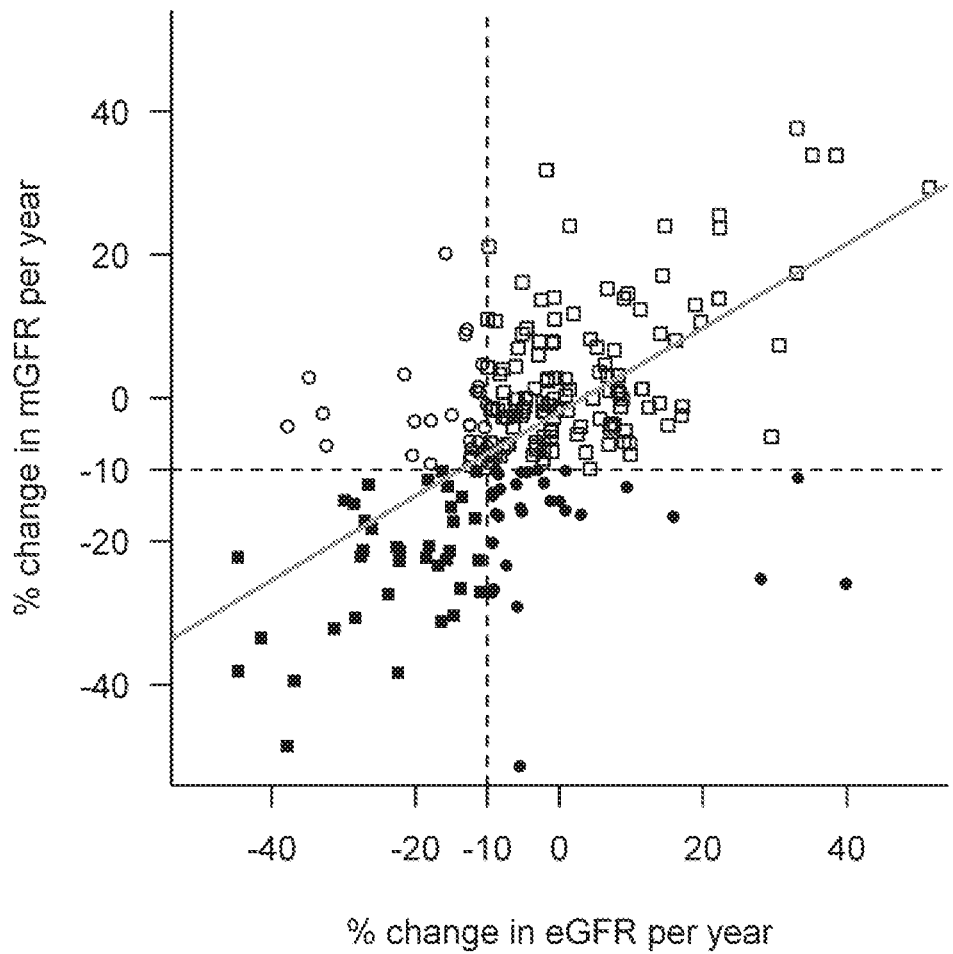
FIG. 1: Best model combining urinary biomarkers to predict 'fast progressor' status in CKD progression. (a): Forest plot showing odds ratios, OR (95% Confidence Interval, CI) of Epidermal Growth Factor (EGF), Monocyte Chemoattractant Protein (MCP1), Transforming Growth Factor-α (TGF-α) and albuminuria in the model; (b): Receiver Operating Characteristic (ROC) curves comparing the area under the curve (AUC) of the best model with the three BMs Epidermal Growth Factor (EGF), Monocyte Chemoattractant Protein (MCP1), Transforming Growth Factor-α (TGF-α) and albuminuria to the AUC of the model without the biomarkers (BMs) but albuminuria alone. Models were adjusted for albuminuria, recruitment centre, history of diabetes and mean mGFR.

Because GDF15 was not found to be associated with progression in the model (OR 0.99 (0.63-1.54)), we tested and observed that when removed from the model, performance criteria of this new model were unaffected (data not shown). Surprisingly, we also observed that NGAL similar to EGF in our model appeared to confer a protective effect (Table 5). This appeared contrary to its individual effect on disease progression where it was associated with an 5 could be simplified by removing GDF15 and NGAL and we provide a final model predicting fast progression with EGF, MCP1 and TGF-α in addition to albuminuria with a c-statistic of 0.84 still superior to that of albumin and the other risk factors (see FIG. 1).

Comparing mGFR and eGFR

Figure 2:
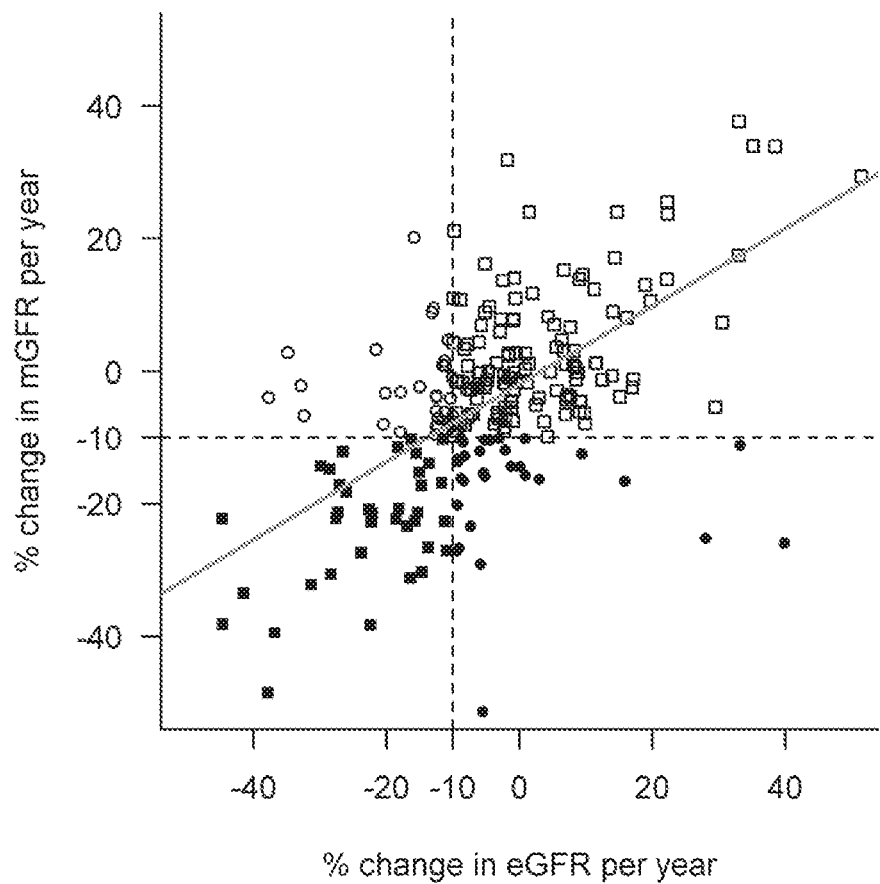
FIG. 2: Percent change in glomerular filtration rate (GFR) per year according to measured GFR (mGFR) and estimated GFR *(eGFR).

Using eGFR instead of mGFR to define CKD progression in our final model gave us different results. Only TGF-α and albumin remained significantly associated with progression in simplified model 5, OR (95% CI) of 1.51(1.07-2.12) and 1.55(1.05-2.27)) respectively but neither EGF nor MCP1, 0.72(0.45-1.15) and 1.21(0.86-1.69) respectively. As expected, correlation between eGFR and mGFR was high (r=0.87) and GFR was overestimated with the formula compared to the gold standard (median bias IQR 2.60 (1.46, 3.76)). Proportion of fast progressors (GFR decline>10%/year) remained the same (29.69%) using either mGFR or eGFR. However, we observed that of the 68 'fast progressors' in the cohort defined by mGFR only 38 (56%) were correctly classified as being 'fast progressors' by using eGFRs giving eGFR quite a low sensitivity for identifying 'fast progressors' (FIG. 2).

Discussion

We did not find an improvement in predictability in our cohort using this model since our outcome measures were different. It would be interesting however to see if the prediction could be ameliorated with the addition of this new biomarker signature.

It is acknowledge that RAAS blockade slows down CKD progression. The observation here that more of the fast-progressors were on ACEI and ARB drugs most likely reflects the clinicians' response to the higher levels of albuminuria in the 'fast progressor' group than a contrary effect of the RAAS blockade in this group42.

This is particularly evident from our results comparing the two techniques as we show here demonstrating the much reduced sensitivity of the eGFR in detecting disease progression. In the context of a discovery observational study such as this one, the well-characterised patient cohort with rigorously mGFRs has been very useful. Having very accurate mGFRs here enabled us correctly classify our patients in their true progressor statuses and as a consequence we could correlate this accurately with the variations in biomarkers in a relatively small cohort and still draw valid significant findings which have not been possible with the less accurate eGFR in which greater numbers of patients would be required.

Since the progress of CKD is a complex pathophysiological process involving many pathways, the need for a combination of several biomarkers (as opposed to a unique biomarker) may be required to make accurate predictions. Although this cohort is relatively small cohort and most of the patients had only two mGFRs over the follow-up period, it has several advantages. The use of the mGFR has already been discussed but in addition this was also an ethnically diverse cohort and contained a good representation of the various pathologies, which account for CKD in registries. We managed to narrow down the number of biomarkers in our final model owing to a degree of redundancy.

In conclusion, we propose TGF-α, EGF, and MCP1 together with albumin and demographic risk factors as a new molecular signature of CKD progression to be potentially used early in the disease process.

REFERENCES

1. Go, A. S., Chertow, G. M., Fan, D., McCulloch, C. E. & Hsu, C.-y. Chronic Kidney Disease and the Risks of Death, Cardiovascular Events, and Hospitalization. *N. Engl. J. Med.* 351, 1296-1305 (2004).
2. Fox, C. S., et al. Associations of kidney disease measures with mortality and end-stage renal disease in individuals with and without diabetes: a meta-analysis. *Lancet* 380, 1662-1673 (2012).
3. Weis, L., et al. Renal Function Can Improve at Any Stage of Chronic Kidney Disease. *PLoS ONE* 8, e81835 (2013).
4. Shankland, S. J. The podocyte's response to injury: Role in proteinuria and glomerulosclerosis. *Kidney Int.* 69, 2131-2147 (2006).
5. Perkins, B. A., et al. Regression of Microalbuminuria in Type 1 Diabetes. *N. Engl. J. Med.* 348, 2285-2293 (2003).
6. Gilbert, R. E., Akdeniz, A., Allen, T. J. & Jerums, G. Urinary transforming growth factor-β in patients with diabetic nephropathy: implications for the pathogenesis of tubulointerstitial pathology. *Nephrol. Dial. Transplant.* 16, 2442-2443 (2001).
7. Riser, B. L., et al. Urinary CCN2 (CTGF) as a possible predictor of diabetic nephropathy: Preliminary report. *Kidney Int.* 64, 451-458 (2003).
8. Gilbert, R. E., et al. Urinary Connective Tissue Growth Factor Excretion in Patients With Type 1 Diabetes and Nephropathy. *Diabetes Care* 26, 2632-2636 (2003).
9. Ghoul, B. E., et al. Urinary Procollagen III Aminoterminal Propeptide (PIIINP): A Fibrotest for the Nephrologist. *Clin. J. Am. Soc. Nephrol.* 5, 205-210 (2010).
10. Soylemezoglu, O., et al. Urinary and serum type III collagen: markers of renal fibrosis. *Nephrol. Dial. Transplant.* 12, 1883-1889 (1997).
11. Van Vliet, A. I., Baelde, H. J., Vleming, L.-J., de Heer, E. & Anthonie Bruijn, J. Distribution of fibronectin isoforms in human renal disease. *J. Pathol.* 193, 256-262 (2001).
12. Guerrot, D., et al. Identification of Periostin as a Critical Marker of Progression/Reversal of Hypertensive Nephropathy. *PLoS ONE* 7, e31974 (2012).
13. Catania, J. M., Chen, G. & Parrish, A. R. Role of matrix metalloproteinases in renal pathophysiologies. *Am. J. Physiol. Renal Physiol.* 292, F905-F911 (2007).
14. Eardley, K. S., et al. The relationship between albuminuria, MCP-1/CCL2, and interstitial macrophages in chronic kidney disease. *Kidney Int.* 69, 1189-1197 (2006).
15. Liu, Y., et al. Urinary Interleukin 18 for Detection of Acute Kidney Injury: A Meta-analysis. *Am. J. Kidney Dis.* 62, 1058-1067 (2013).
16. Parikh, C. R., Abraham, E., Ancukiewicz, M., Edelstein, C. L. & Network, f.t.A.R.D.S. Urine IL-18 Is an Early Diagnostic Marker for Acute Kidney Injury and Predicts Mortality in the Intensive Care Unit. *J. Am. Soc. Nephrol.* 16, 3046-3052 (2005).
17. Shlipak, M. G., Fried, L. F., Cushman, M. & et al. Cardiovascular mortality risk in chronic kidney disease: Comparison of traditional and novel risk factors. *JAMA* 293, 1737-1745 (2005).
18. Yoshino, J., Monkawa, T., Tsuji, M., Hayashi, M. & Saruta, T. Leukemia Inhibitory Factor Is Involved in Tubular Regeneration after Experimental Acute Renal Failure. *J. Am. Soc. Nephrol.* 14, 3090-3101 (2003).
19. Lajer, M., Jorsal, A., Tarnow, L., Parving, H. & Rossing, P. Plasma Growth Differentiation Factor-15 Independently Predicts All-Cause and Cardiovascular Mortality As Well As Deterioration of Kidney Function in Type 1 Diabetic Patients With Nephropathy. *Diabetes Care* 33, 1567-1572 (2010).
20. Lautrette, A., et al. Angiotensin II and EGF receptor cross-talk in chronic kidney diseases: a new therapeutic approach. *Nat. Med.* 11, 867-874 (2005).
21. Viau, A., et al. Lipocalin 2 is essential for chronic kidney disease progression in mice and humans. *J. Clin. Invest.* 120, 4065-4076 (2010).
22. Eremina, V., et al. Glomerular-specific alterations of VEGF-A expression lead to distinct congenital and acquired renal diseases. *J. Clin. Invest.* 111, 707-716 (2003).
23. Sakamoto, I., et al. Lymphatic vessels develop during tubulointerstitial fibrosis. *Kidney Int.* 75, 828-838 (2009).
24. Kamijo, A., et al. Clinical evaluation of urinary excretion of liver-type fatty acid-binding protein as a marker for the monitoring of chronic kidney disease: a multicenter trial. *J. Lab. Clin. Med.* 145, 125-133 (2005).
25. Nakamura, T., et al. Effect of Pitavastatin on Urinary Liver-Type Fatty Acid-Binding Protein Levels in Patients With Early Diabetic Nephropathy. *Diabetes Care* 28, 2728-2732 (2005).
26. Von Eynatten, M., et al. Urinary L-FABP and anaemia: distinct roles of urinary markers in type 2 diabetes. *Eur. J. Clin. Invest.* 40, 95-102 (2010).
27. Humphreys, B. D., et al. Chronic epithelial kidney injury molecule-1 expression causes murine kidney fibrosis. *J. Clin. Invest.* 123, 4023-4035 (2013).
28. Rall, L. B., et al. Mouse prepro-epidermal growth factor synthesis by the kidney and other tissues. *Nature* 313, 228-231 (1985).

29. Herget-Rosenthal, S., van Wijk, J. A. E., Bröcker-Preuss, M. & Bökenkamp, A. Increased urinary cystatin C reflects structural and functional renal tubular impairment independent of glomerular filtration rate. *Clin. Biochem.* 40, 946-951 (2007).
30. Vyletal, P., Bleyer, A. J. & Kmoch, S. Uromodulin Biology and Pathophysiology—An Update. *Kidney Blood Press. Res.* 33, 456-475 (2010).
31. Moranne, O., et al. Timing of onset of CKD-related metabolic complications. *J. Am. Soc. Nephrol.* 20, 164-171 (2009).
32. Levey, A. S., et al. A More Accurate Method To Estimate Glomerular Filtration Rate from Serum Creatinine: A New Prediction Equation. *Ann. Intern. Med.* 130, 461-470 (1999).
33. Tangri, N., Stevens, L. A., Griffith, J. & et al. A predictive model for progression of chronic kidney disease to kidney failure. *JAMA* 305, 1553-1559 (2011).
34. Stevens, L. A., Greene, T. & Levey, A. S. Surrogate End Points for Clinical Trials of Kidney Disease Progression. *Clin. J. Am. Soc. Nephrol.* 1, 874-884 (2006).
35. Coresh, J., et al. Decline in estimated glomerular filtration rate and subsequent risk of end-stage renal disease and mortality. *JAMA* 311, 2518-2531 (2014).
36. Laouari, D., et al. TGF-α Mediates Genetic Susceptibility to Chronic Kidney Disease. *J. Am. Soc. Nephrol.* 22, 327-335 (2011).
37. Meng, X.-M., Nikolic-Paterson, D. J. & Lan, H. Y. Inflammatory processes in renal fibrosis. *Nat Rev Nephrol* 10, 493-503 (2014).
38. Vianna, H., et al. Cytokines in chronic kidney disease: potential link of MCP-1 and dyslipidemia in glomerular diseases. *Pediatr. Nephrol.* 28, 463-469 (2013).
39. Bolignano, D., et al. Neutrophil Gelatinase-Associated Lipocalin (NGAL) and Progression of Chronic Kidney Disease. *Clin. J. Am. Soc. Nephrol.* 4, 337-344 (2009).
40. Liu, K. D., et al. Urine neutrophil gelatinase-associated lipocalin levels do not improve risk prediction of progressive chronic kidney disease. *Kidney Int.* 83, 909-914 (2013).
41. Rau, S., et al. Neutrophil gelatinase-associated lipocalin and end-stage renal disease: it is not all about the kidneys! *Eur. J. Clin. Invest.* 43, 816-820 (2013).
42. Remuzzi, G., Perico, N., Macia, M. & Ruggenenti, P. The role of renin-angiotensin-aldosterone system in the progression of chronic kidney disease. *Kidney Int.* 68, S57-S65 (2005).
43. Ruggenenti, P., et al. Measuring and Estimating GFR and Treatment Effect in ADPKD Patients: Results and Implications of a Longitudinal Cohort Study. *PLoS ONE* 7, e32533 (2012).
44. Suthanthiran, M., et al. Circulating transforming growth factor-[beta]1 levels and the risk for kidney disease in African Americans. *Kidney Int.* 76, 72-80 (2009).

---

What is claimed is:

1. A method for the prediction and treatment of fast progression of chronic kidney disease in a subject, comprising the steps of:
 a) evaluating expression of biomarkers in a biological sample obtained from said subject,
 wherein the evaluating step includes quantifying the expression of the biomarkers to obtain their expression values in the biological sample obtained from said subject and comparing said expression values to corresponding control values, and
 wherein said biomarkers comprise transforming growth factor alpha (TGF-α), epidermal growth factor (EGF), monocyte chemoattractant protein 1 (MCP1), and Neutrophil Gelatinase-associated Lipocalin (NGAL), and further biomarkers selected from the group consisting of Growth and Differentiation Factor 15 (GDF15), Cystatin C, Fatty Acid Binding Protein (FABP), Fibronectin, Kidney Injury Molecule 1 (KIM1), Osteopontin, Tissue Inhibitor of Metalloprotease 1 (TIMP1), Uromodulin, Interleukin-6 (IL6), Leukemia Inhibitory Factor (LIF), Matrix Metallopeptidase 9 (MMP9) and Vascular Endothelial Growth Factor A (VEGFA); and
 b) administering an effective amount of a therapeutic agent to the subject to treat chronic kidney disease.

2. The method of claim 1, wherein an expression value of TGF-α above a control value, and/or an expression value of EGF below a control value and/or an expression value of MCP1 above a control value and/or an expression value of NGAL above a control value, indicates that the subject is at increased risk of fast progression.

3. The method of claim 2, wherein said biological sample is urine or serum sample.

4. The method of claim 3, wherein a subject predicted of fast progression is a subject who is at risk of losing more than 10% of the baseline measured glomerular filtration rate (mGFR) per year.

5. The method of claim 2, wherein said expression is protein expression as quantified in an immunoassay.

* * * * *